US008895310B2

(12) United States Patent
Keβeler et al.

(10) Patent No.: US 8,895,310 B2
(45) Date of Patent: Nov. 25, 2014

(54) L-RHAMNOSE-INDUCIBLE EXPRESSION SYSTEMS

(75) Inventors: Maria Keβeler, Mannheim (DE); Thomas Zelinski, Neuleiningen (DE); Bernhard Hauer, Fußgönheim (DE)

(73) Assignee: BASF SE, Ludwigshafen (DE)

( * ) Notice: Subject to any disclaimer, the term of this patent is extended or adjusted under 35 U.S.C. 154(b) by 2063 days.

(21) Appl. No.: 10/537,075

(22) PCT Filed: Nov. 27, 2003

(86) PCT No.: PCT/EP03/13367
§ 371 (c)(1),
(2), (4) Date: Jun. 1, 2005

(87) PCT Pub. No.: WO2004/050877
PCT Pub. Date: Jun. 17, 2004

(65) Prior Publication Data
US 2006/0014291 A1   Jan. 19, 2006

(30) Foreign Application Priority Data
Dec. 2, 2002 (DE) .................... 102 56 381

(51) Int. Cl.
C12N 15/63 (2006.01)
C12N 15/70 (2006.01)
C12N 15/74 (2006.01)
C12N 1/21 (2006.01)

(52) U.S. Cl.
CPC ............... *C12N 15/63* (2013.01); *C12N 15/70* (2013.01)
USPC ...................... 435/488; 435/252.33

(58) Field of Classification Search
CPC .............. C12N 15/63; C12N 15/70
USPC ...................... 435/41, 488, 252.33
See application file for complete search history.

(56) References Cited

U.S. PATENT DOCUMENTS

| 5,028,530 | A |   | 7/1991  | Lai et al. |
| 5,576,195 | A |   | 11/1996 | Robinson et al. |
| 5,837,509 | A | * | 11/1998 | Israelsen et al. ............. 435/91.1 |
| 5,846,818 | A |   | 12/1998 | Robinson et al. |
| 6,869,783 | B1 |  | 3/2005  | Ress-Löschke et al. |

FOREIGN PATENT DOCUMENTS

| CA | 2 389 064    | 5/2001  |
| DE | 198 48 129   | 4/2000  |
| WO | WO-00/23577  | 4/2000  |
| WO | WO-0123582 A1 | 4/2001 |
| WO | WO-01/32890  | 5/2001  |
| WO | WO-01/73082  | 10/2001 |

OTHER PUBLICATIONS

Wilms, B. et al., "High-Cell-Density Fermentation for Production of L-*N*-Carbamoylase Using an Expression System Based on the *Escherichia coli* rhaBAD Promoter", Biotechnology and Bioengineering, (Apr. 20, 2001), vol. 73, No. 2 , pp. 95-103.
Bulawa, C. et al., "Isolation and Characterization of *Escherichia coli* Strains Defective in CDP-diglyceride Hydrolase", Journal of Biological Chemistry, (Sep. 25, 1984), vol. 259, No. 18 , pp. 11257-11264.
Haldimann, A. et al., "Use of New Methods for Construction of Tightly Regulated Arabinose and Rhamnose Promoter Fusions in Studies of the *Escherichia coli* Phosphate Regulon", Journal of Bacteriology, (Mar. 1998), vol. 180, No. 5, pp. 1277-1286.
Egan, S. et al., "A Regulatory Cascade in the Induction of *rhaBAD*", Journal of Molecular Biology, (1993), vol. 234, No. 1, pp. 87-98.
Moralejo, P. et al., "Sequencing and Characterization of a Gene Cluster Encoding the Enzymes for L-Rhamnose Metabolism in *Escherichia coli*", Journal of Bacteriology, (Sep. 1993), vol. 175, No. 17, pp. 5585-5594.
Tobin, J. et al., "Transcription from the *rha* Operon $p_{sr}$ Promoter", Journal of Molecular Biology (1990), 211, pp. 1-4.
Chen, Y.-M. et al., "Cross-Induction of the L-Fucose System by L-Rhamnose in *Escherichia coli*", Journal of Bacteriology (Aug. 1987), vol. 169, No. 8, pp. 3712-3719.
Stumpp, T., et al., "Ein Neues, L-Rhamnose-Induzierbares Expressionssystem für *Escherichia coli*", Biospektrum, Spektrum Akademischer Verlag, DE, 2000, vol. 6, No. 1, pp. 33-36.
Al-Zarban, S. et al. "Positive Control of the $_L$-Rhamnose Genetic System in *Salmonella typhimurium* LT2", Journal of Bacteriology, 1984, vol. 158, No. 2, pp. 603-608.
Takagi, Y., et al. "The Metabolism of $_L$-Rhamnose in *Escherichia coli*. I. $_L$-Rhamnose Isomerase", Biochimica et Biophysica Acta, 1964, vol. 92, pp. 10-17.

* cited by examiner

*Primary Examiner* — Catherine Hibbert
(74) *Attorney, Agent, or Firm* — Drinker Biddle & Reath LLP

(57) ABSTRACT

The present invention relates to methods for expressing nucleic acid sequences in prokaryotic host cells, where at least one DNA construct which is capable of episomal replication in a host cell and which comprises a nucleic acid sequence to be expressed under the transcriptional control of an L-rhamnose-inducible promoter, where the promoter is heterologous with regard to the nucleic acid sequence, is introduced into the host cell and the expression of he nucleic acid sequence is induced by addition of L-rhamnose, wherein the prokaryotic host cell is at least deficient with regard to an L-rhamnose isomerase.

15 Claims, 1 Drawing Sheet

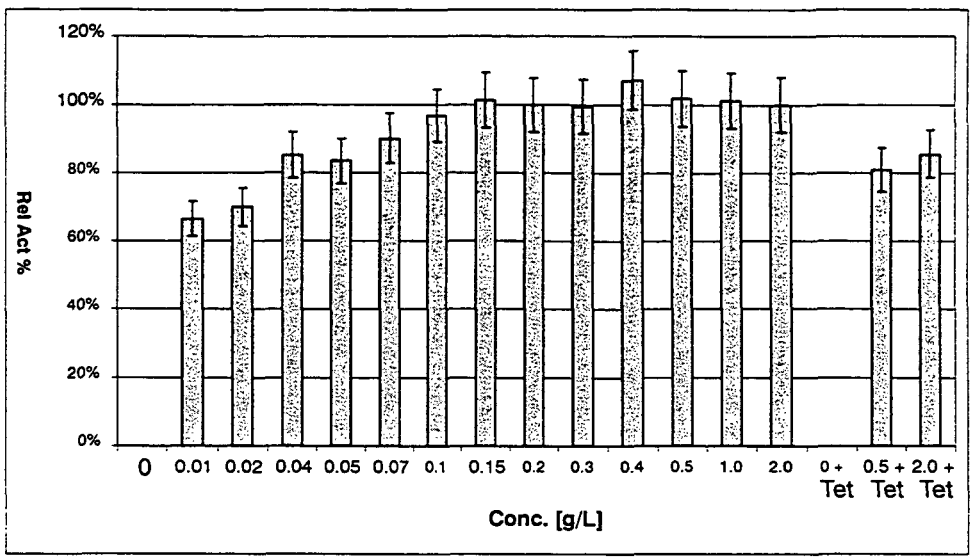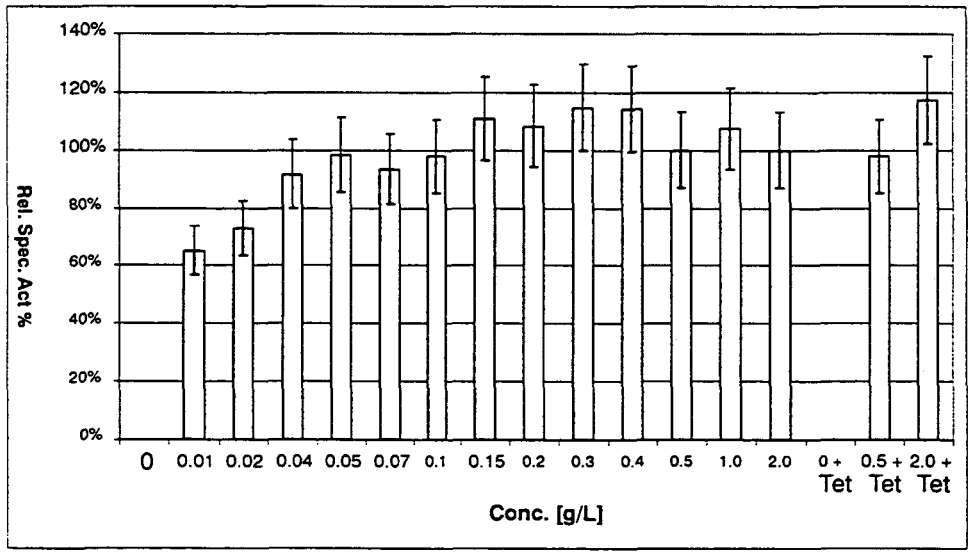

ative inductor (for example lactose) or an artificial inductor (for example isopropyl-β-D-thiogalactopyranoside; IPTG), thus initiating expression. In contrast to lactose, IPTG cannot be metabolized and thus ensures long-term induction. A further example of these inducible promoters is the arabinose-inducible araB promoter (U.S. Pat. No. 5,028,530; Guzman L M et al. (1995) J Bacteriol 177:4121-4130).

L-RHAMNOSE-INDUCIBLE EXPRESSION SYSTEMS

RELATED APPLICATIONS

This application is a national stage application (under 35 U.S.C. 371) of PCT/EP2003/013367 filed Nov. 27, 2003 which claims benefit to German application 102 56 381.0 filed Dec. 2, 2002.

The present invention relates to methods for expressing nucleic acid sequences in prokaryotic host cells, where at least one DNA construct which is capable of episomal replication in said host cells and which comprises a nucleic acid sequence to be expressed under the transcriptional control of an L-rhamnose-inducible promoter, where said promoter is heterologous with regard to said nucleic acid sequence, is introduced into said host cells and the expression of said nucleic acid sequence is induced by addition of L-rhamnose, wherein the prokaryotic host cell is at least deficient with regard to an L-rhamnose isomerase. The invention furthermore relates to prokaryotic host cells which are at least deficient with regard to an L-rhamnose isomerase and which comprise at least one DNA construct which is capable of replication in said host cell and which comprises a nucleic acid to be expressed under the transcriptional control of an L-rhamnose-inducible promoter, where said promoter is heterologous with regard to said nucleic acid sequence.

The heterologous expression of genes is an economical way of producing enzymes and other proteins for pharmaceutical and industrial purposes. Said expressions are still predominantly carried out using strains of Escherichia coli. A multiplicity of systems which rely on different host organisms and gene expression cassettes are known for the production of recombinant proteins. Although a large number of systems and methods for expressing recombinant proteins in microbiological systems have been described, the expression systems for Gram-negative bacteria such as Escherichia coli are based on a very limited range of bacterial promoters. Most widely used are the lactose promoter [lac] (Yanisch-Perron et al. (1985) Gene 33: 103-109) and the tryptophan promoter [trp] (Goeddel et al. (1980) Nature (London) 287: 411-416) and hybrid promoters of the above [lac and trp] (Brosius (1984) Gene 27:161-172; Amanna & Brosius (1985) Gene 40: 183-190). Further examples are the PL and PR promoters of λ phage (Elvin et al. (1990) Gene 37:123-126), the Phage T7 promoter (Tabor & Richardson (1998) Proc Natl Acad Sci USA 82:1074-1078) and the alkaline phosphatase promoter [pho] (Chang et al. (1986) Gene 44:121-125).

Heterologous expression entails various problems such as, for example, the toxicity of the gene product, unduly low expression rates or the formation of insoluble protein aggregates ("inclusion bodies"). Many of the above-described promoters are unsuitable for applications where the recombinant protein to be expressed has a toxic effect on the host in question. The strictest possible regulation of expression is desirable in these cases. Promoter systems which can be employed for this purpose are what are known as inducible promoter systems, which can be induced by means of addition of an inductor or another exogenous stimulus (for example heat). As a rule, said inducible promoter systems consist of a promoter/regulator combination, where the regulator is for example a protein which, in combination with an exogenous stimulus, induces the transcription starting from the promoter in question. An example which may be mentioned is the combination of a promoter with a repressor such as, for example, the lac repressor (Studier F W et al. (1990) Methods in Enzymol 185:60-89; Dubendorff J W & Studier F W (1991) J Mol Biol 219:45-59). The repressing effect of this repressor can be removed by addition of a natural inductor (for example lactose) or an artificial inductor (for example isopropyl-β-D-thiogalactopyranoside; IPTG), thus initiating expression. In contrast to lactose, IPTG cannot be metabolized and thus ensures long-term induction. A further example of these inducible promoters is the arabinose-inducible araB promoter (U.S. Pat. No. 5,028,530; Guzman L M et al. (1995) J Bacteriol 177:4121-4130).

IPTG and other synthetic inductors are very expensive and, in some cases, have an adverse effect on the growth of the organisms, which makes an application on the industrial scale uneconomic.

While, as a rule, physiological inductors such as amino acids (for example tryptophan) and sugars (arabinose) are cheaper, they are metabolized by the organism so that substantial amounts must be added and/or fed subsequently when cells are grown, in particular in the case of high-density cell fermentations. Moreover, metabolites of these compounds may later also be harmful for the culture, for example when acetate is produced from sugars.

WO 01/73082 describes a method for expressing recombinant proteins under the control of the inducible araB promoter in an E. coli host organism with deficiency for the active transport of the inductor arabinose. The advantage here is said to be that no active transport, but only passive transport (by means of diffusion), can take place. This means better control for the intracellular arabinose concentration and thus also expression induction. In some of the examples stated, an E. coli strain (E104) with deficiency in the arabinose-metabolizing enzymes ribulokinase (AraB) and L-ribulose-5-phosphate 4-epimerase (AraD) is employed. In accordance with the expression data, however, this deficiency has no substantial effect on the expression levels. The arabinose-inducible system has various disadvantages:

a) Arabinose has a growth-inhibitory effect on the bacterial culture from concentrations of as little as 0.1 mM and above, which can be compensated for only to a certain extent, even when using the method described in WO 01/73082 (cf. Table 4, WO 01/73082).

b) The arabinose-inducible promoter is not entirely inactive in the absence of arabinose, but has a fairly high basal activity (cf. Table 5, WO 01/73082).

c) The quality of the recombinant proteins expressed depends on the cell density and decreases with increasing cell densities (De Lisa M P et al. (1999) Biotechnol Bioeng 65:54-64).

The Escherichia coli strain JB1204 (CGSC6999, Bulawa & Raetz (1984) J Biol Chem 259:11257-11264), which has the transposon insertion "rha-14::Tn10", is described, but no detailed information on the sequence or function of "rha-14" is provided.

The uptake and metabolization of L-rhamnose in bacteria such as E. coli is described. L-Rhamnose is taken up into the cells via an active transport system (RhaT), converted into L-rhamnulose by an isomerase (RhaA), and L-rhamnulose is then phosphorylated further by rhamnulose 1-phosphatase (RhaB) and hydrolyzed by an aldolase (RhaD) to give dihydroxyacetone phosphate and lactaldehyde. The genes rha-BAD form an operon and are transcribed with the aid of what is known as the rhaP$_{BAD}$ promoter. In comparison with other systems, the rhamnose system is distinguished by the fact that two activators RhaS and RhaR are required for regulation. These two form a transcriptional unit and are transcribed in the opposite direction to rhaBAD. When L-rhamnose is present, RhaR binds to the rhaP$_{RS}$ promoter and initiates its own expression as well as the expression of RhaS. RhaS, in turn, once activated by L-rhamnose, binds as effector to the rhaP$_{BAD}$ promoter and the separate rhaP$_T$ promoter of the rhaT gene and activates the transcription of the structural gene (Moralejo P et al. (1993) J Bacteriol 175:5585-5594; Tobin J F et al. (1990) J Mol Biol 211:1-4; Chen Y M et al. (1987) J Bacteriol 169:3712-3719; Egan S M et al. (1993) J Mol Biol 243:87-98). The combination of two activators causes an unusually strict expressional control by the rhaP$_{BAD}$ promoter. A comparison between the arabinose-inducible araB promoter and the rhamnose-inducible rhaP$_{BAD}$ promoter shows that the latter is subjected to substantially stricter regulation and, in the absence of the inductor rhamnose, virtually represents a zero phenotype (Haldimann A et al. (1998) J Bacteriol 180(5):1277-1286).

WO 01/32890 describes the production of L-pantolactone hydrolase using *Escherichia coli* TG1 pDHE681 or derivatives, where L-rhamnose is employed as inductor for the gene expression of the enzyme. Since L-rhamnose is metabolized well by *E. coli*, the L-rhamnose converted must be supplemented by feeding in. This makes the experimentation considerably more complicated and increases the costs for the culture medium.

Furthermore described are expression systems for the fermentation under high cell densities using the L-rhamnose-inducible rhaBAD promoter and an *E. coli* strain with a site-specifically introduced deficiency in L-rhamnulose kinase (rhaB) (Stumpp T et al. (2000) Biospectrum 6(1):33-36; Wilms B et al. (2001) Biotechnol Bioeng 73(2): 95-103). RhaB was deliberately selected here since it is the first irreversible step in the metabolization of L-rhamnose (cf. Wilms B et al. (2001) Biotechnol Bioeng 73(2) p. 98, left column, lines 4-8). Optimal induction can be achieved in these systems using L-rhamnose concentrations of 2 g/L (cf. Wilms B et al. (2001) Biotechnol Bioeng 73(2) p. 102, left column, 2nd paragraph, lines 1-4). These concentrations are still very high. With an average L-rhamnose price of approximately 100 euros/kg, a 10 m$^3$ fermenter would mean that 2000 euros are spent on L-rhamnose alone.

Furthermore described are tightly-regulated rhamnose-inducible expression systems where the rhamnose operon (BAD), which is located behind the endogenous rhaP$_{BAD}$ promoter, is replaced by the PhoB gene (transcription activator) by means of homologous recombination (Haldimann A et al. (1998) J Bacteriol 180(5):1277-1286). While the system described herein is well suited to regulator studies since very tight regulation is ensured, it is less suitable for overexpression—in particular under high-density cell culture conditions—since in each case only one copy of the rhaP$_{BAD}$ promoter-controlled expression cassette can be introduced as the result of the replacement of the chromosomal rhamnose operon. Furthermore, the replacement of genes by homologous recombination is complicated and requires a tedious selection and characterization of suitably modified organisms. This makes the method described unsuitable for routine purposes.

It was an object to provide an improved method for expressing nucleic acids—and preferably recombinant proteins—where small L-rhamnose quantities give high expression levels. This object is achieved by the present invention.

A first aspect of the invention relates to methods for expressing nucleic acid sequences in prokaryotic host cells, where a) at least one DNA construct which is capable of episomal replication in said host cells and which comprises a nucleic acid sequence to be expressed under the transcriptional control of an L-rhamnose-inducible promoter, where said promoter is heterologous with regard to said nucleic acid sequence, is introduced into said host cells and b) prokaryotic host cells which comprise said DNA construct in episomal form are selected and c) the expression of said nucleic acid sequence is induced by addition of L-rhamnose to a culture of said selected host cells, wherein the prokaryotic host cell is at least deficient with regard to L-rhamnose isomerase.

In a preferred embodiment, the expression of the nucleic acid sequence to be expressed causes the production of a protein encoded by said nucleic acid sequence so that the method according to the invention for the production of recombinant proteins can be employed.

In a furthermore preferred embodiment, an additional deficiency may be present in one or more further L-rhamnose-metabolizing, or -transporting, protein(s).

A further aspect of the invention relates to a prokaryotic host cell which is at least deficient with regard to L-rhamnose isomerase and which comprises at least one DNA construct which is capable of replication in said host cell and which comprises a nucleic acid sequence to be expressed under the transcriptional control of an L-rhamnose inducible promoter, where said promoter is heterologous with regard to said nucleic acid sequence.

In a preferred embodiment, the prokaryotic host cell according to the invention may have an additional deficiency in one or more further L-rhamnose-metabolizing, or -transporting, protein(s).

Furthermore, the invention relates to a method for the production of recombinant proteins, enzymes and other fine chemicals such as, for example, chiral carboxylic acids, using one of the prokaryotic host cells according to the invention or a preparations thereof.

The method according to the invention has various advantages:

1. It is simple to employ since the expression strain in question can be generated, starting from a host strain, by simple transformation without an insertion into the genome by means of homologous recombination (as by Haldimann A et al. (1998) J Bacteriol 180(5):1277-1286) and a laborious selection of correctly modified organisms being required.
2. The expression cassettes and expression vectors provided within the scope of the invention are easy to handle. The rhaP$_{BAD}$ promoter, which is employed by way of example, has a length of just 123 base pairs.
3. Since L-rhamnose is metabolized by *E. coli*, in particular in the case of C-source-limited fermentations, standard methods result in a high L-rhamnose consumption (feeding) and thus high medium costs. Since the method according to the invention has a low L-rhamnose requirement (<1% in comparison with L-rhamnose-metabolizing strains), the costs for the fermentation medium, and thus the production of biocatalyst, are reduced substantially. By providing the method according to the invention, recombinant proteins (for example nitrilase, L-pantolactone hydrolase) can be produced by high-density cell fermentation (for example of the *E. coli* TG10 strains provided) without constantly feeding rhamnose.
4. The regulation of the system described proved to be extraordinarily tight and continued to provide maximum induction even at very low concentrations of the inductor L-rhamnose of up to 0.05 g/l, while no promoter activity whatsoever was detected in the absence of the inductor. Thus, the system is also outstandingly suitable for the expression of potentially toxic proteins and makes possible an inexpensive production, in particular under industrial conditions, since only low L-rhamnose concentrations are required.

For the purposes of the present invention, "prokaryotic host cell" or "prokaryotic host organism" means Gram-positive or Gram-negative bacteria, but in particular those Gram-positive or Gram-negative bacteria which are naturally capable of metabolizing L-rhamnose as carbon source. L-Rhamnose can be utilized as carbon source by most prokaryotic organisms.

Preferably, prokaryotic host cell or prokaryotic host organism means all genera and species of the Enterobacteriaceae and the families Actinomycetales, very especially preferably the Enterobacteriaceae species *Escherichia, Serratia, Proteus, Enterobacter, Klebsiella, Salmonella, Shigella, Edwardsielle, Citrobacter, Morganella, Providencia* and *Yersinia*.

Furthermore preferred are the species *Pseudomonas, Burkholderia, Nocardia, Acetobacter, Gluconobacter, Corynebacterium, Brevibacterium, Bacillus, Clostridium, Cyanobacter, Staphylococcus, Aerobacter, Alcaligenes, Rhodococcus* and *Penicillium*.

Most preferred are *Escherichia* species, in particular *Escherichia coli*.

"L-Rhamnose-inducible promoter" generally means all those promoters which have a higher expression activity in the presence of L-rhamnose than in the absence of L-rhamnose. Expression in the presence of L-rhamnose is at least twice as high, preferably at least five times as high, very especially preferably at least ten times as high, most preferably at least one hundred times as high as in the absence of L-rhamnose. Nucleic acid sequences which are preferably employed for the purposes of determining the expression level are those nucleic acid sequences in functional linkage with the promoter to be tested which encode readily quantifiable proteins. Very especially preferred in this context are reporter proteins (Schenborn E, Groskreutz D (1999) Mol Biotechnol 13(1): 29-44) such as "green fluorescence protein" (GFP) (Chui W L et al. (1996) Curr Biol 6:325-330; Leffel S M et al. (1997) Biotechniques 23(5):912-8), chloramphenicol transferase, luciferase (Millar et al. (1992) Plant Mol Biol Rep 10:324-414), β-glucuronidase or β-galactosidase.

In this context, the L-rhamnose concentration in the medium can generally be in the range of from approximately 0.0001 g/l to approximately 50 g/l, preferably 0.001 g/l to 5 g/l, especially preferably 0.01 g/l to 0.5 g/l.

Especially preferred is the rhaP$_{BAD}$ promoter from the L-rhamnose operon rhaBAD in *E. coli* (Egan & Schleif (1994) J Mol Biol 243:821-829) and its functional equivalents from other prokaryotic organisms, in particular organisms of the Enterobacteriaceae family.

Very especially preferred promoters are those which comprise at least one RhaS binding element as shown in SEQ ID NO: 5 or a functional equivalent thereof, and also a functionally equivalent fragment of the above.

Especially preferred promoters are those which comprise a sequence as shown in SEQ ID NO: 2, 3 or 4 and functional equivalents thereof, and also functional equivalent fragments of the above.

Functional equivalents to a promoter comprising a sequence as shown in SEQ ID NO: 2, 3, 4 or 5 preferably comprise those promoters which
a) have essentially the same promoter activity as the promoter comprising a sequence as shown in SEQ ID NO: 2, 3, 4 or 5 and
b) have at least 50%, preferably 70%, by preference at least 80%, especially preferably at least 90%, very especially preferably at least 95%, most preferably 99% homology with the sequence of said promoter, where the homology extends over a length of at least 30 base pairs, preferably at least 50 base pairs, especially preferably at least 100 base pairs.

Functional equivalents to a promoter comprising a sequence as shown in SEQ ID NO: 2, 3, 4 or 5 means in particular natural or artificial mutations of said promoter and homology sequences and functionally equivalent sequences from other organisms, preferably from other prokaryotic organisms, in particular organisms of the Enterobacteriaceae family, which have essentially the same promoter activity as said promoter.

"Essentially the same promoter activity" means the inducibility of the expression activity by L-rhamnose in accordance with the above general definition for L-rhamnose-inducible promoters.

As described above, the RhaR protein binds to the rhaP$_{RS}$ promoter in the presence of L-rhamnose and initiates its own expression as well as the expression of RhaS. RhaS, in turn, binds to the rhaP$_{BAD}$ promoter, with L-rhamnose as effector, and now activates the rhaP$_{BAD}$ promoter and thus the transcription of the nucleic acid sequences regulated by said promoter. This upstream regulatory unit—consisting of RhaR, RhaS and the rhaP$_{RS}$ promoter—can be provided naturally by the prokaryotic host organism, inserted into the genome of the latter by recombinant methods, or else be provided by means of the DNA construct employed within the scope of the invention. One promoter cassette which is suitable in this context is the sequence described by SEQ ID NO: 1.

If the L-rhamnose uptake required for induction in the cell should be insufficient, it may be advantageous in organisms which, for example, naturally express no L-rhamnose transporter, to transgenically express the latter. However, experience to date shows that the active rhamnose transport should not represent the limiting factor for the efficiency of the expression system according to the invention.

"L-Rhamnose isomerase" generally means all those proteins which are capable of converting L-rhamnose into a different hexose.

Preferably, L-rhamnose isomerase means proteins which are capable of converting L-rhamnose into L-rhamnulose (EC 5.3.1.14).

Especially preferred is the RhaA gene from organisms of the Enterobacteriaceae family, in particular *E. coli*. Most preferably, L-rhamnose isomerase means the protein as shown in SEQ ID NO: 9 and homologous sequences from other organisms, preferably from other prokaryotic organisms.

Functional equivalent to the L-rhamnose isomerase as shown in SEQ ID NO: 9 preferably comprises those sequences which
a) have essentially the same enzyme activity as the L-rhamnose isomerase as shown in SEQ ID NO: 9 and
b) have at least 50%, preferably 70%, by preference at least 80%, especially preferably at least 90%, very especially preferably at least 95%, most preferably 99% homology with the sequence of the L-rhamnose isomerase as shown in SEQ ID NO: 9, where the homology extends over a length of at least amino acids, preferably at least 50 amino acids, especially preferably at least 100 amino acids, very especially preferably at least 200 amino acids, most preferably over the entire length of the protein.

Besides the L-rhamnose isomerase, further deficiencies with regard to genes which have a function in the metabolization of L-rhamnose may also be present. Deficiencies which may be mentioned in particular in this context are rhamnulose 1-phosphatase/kinase deficiency (e.g. RhaB; for example described by SEQ ID NO: 11), a rhamnulophosphate aldolase deficiency (e.g. RhaD; for example described by SEQ ID NO: 13) or a deficiency in at least one regulatory element which controls the expression of the abovementioned proteins (such as, for example, promoter, regulator or similar).

Under certain circumstances, it can furthermore be advantageous to generate a deficiency in an active rhamnose transport system (e.g. RhaT; for example described by SEQ ID NO: 19).

"Deficiency" with regard to an L-rhamnose isomerase or another enzyme of L-rhamnose uptake/metabolization means the essentially complete inhibition or blocking of the expression of the target gene in question or of the mRNA derived therefrom and/or of the protein product encoded thereby or the modification of the protein sequence of the gene product in such a manner that its function and/or activity is essentially inhibited or modified in such a way that L-rhamnose can essentially no longer be converted, this inhibition or blocking being based on different cell-biological mechanisms.

Inhibition or blocking for the purposes of the invention comprises in particular the quantitative reduction of an mRNA expressed by the target gene and/or of the protein product encoded thereby down to an essentially complete absence thereof. In this context, the expression, in a cell or an organism, of a certain mRNA and/or of the protein product included thereby is preferably reduced by more than 50%, especially preferably by more than 80%, very especially preferably by more than 90%, most preferably by more than 95% in comparison with the same cell or organism which have not been subjected to the method. Very especially preferably, reduction means the complete inactivation of an endogenous gene (knock-out mutation).

Inhibition or blocking can be based on different mechanisms. Preferably, inhibition or blocking are based on a mutation of the target gene in question, it being possible for the mutation to consist in a substitution, deletion and/or addition of one or more nucleotide(s). Especially preferred is an inhibition or blocking by means of transposon-aided mutagenesis or by means of site-specific knock-out.

The reduction can be determined by methods with which the skilled worker is familiar. Thus, the reduction of the protein quantity can be determined for example by an immunological detection of the protein. Furthermore, it is possible to employ biochemical techniques such as Northern hybridization, nuclease protection assay, reverse transcription (quantitative RT-PCR), ELISA (enzyme linked immunosorbent assay), Western blotting, radioimmunoassay (RIA) or other immunoassays and fluorescence-activated cell analysis (FACS). Depending on the type of the produced protein product, the activity of the latter, or the influence of the phenotype of the organism or the cell, may also be determined.

"Protein quantity" means the amount of a particular polypeptide in an organism, a tissue, a cell or a cell compartment.

"Reduction" of the protein quantity means the reduction of the amount of a particular polypeptide in an organism, a tissue, a cell or a cell compartment in comparison with the wild type of the same genus and species to which this method has not been applied, under otherwise identical framework conditions (such as, for example, culture conditions, age, nutrient supply and the like). In this context, the reduction amounts to at least 50%, preferably at least 70%, especially preferably at least 90%, very especially preferably at least 95%, most preferably at least 99%. Methods for determining the protein quantity are known to the skilled worker. Examples which may be mentioned are: the micro-Biuret method (Goa J (1953) Scand J Clin Lab Invest 5:218-222), the Folin-Ciocalteu method (Lowry O H et al. (1951) J Biol Chem 193:265-275) or measuring the adsorption of CBB G-250 (Bradford M M (1976) Analyt Biochem 72:248-254).

The reduction of the L-rhamnose isomerase activity can be determined in particular by means of enzymatic assay systems. Suitable assay systems are known to the skilled worker (Bhuiyan S H et al. (1997) J Ferment Bioeng 84(4):319-323).

"DNA construct which is capable of episomal replication in prokaryotic host cells" means all those DNA constructs which differ from the chromosomal DNA of said host cell and which exist in parallel with the former in said host cell and are capable of replicating in said host cell using homologous or other replication mechanisms (for example replication mechanisms which are encoded via the DNA construct itself). The DNA construct can constitute a single- or double-stranded DNA structure. Preferably, the DNA construct has a double-stranded DNA structure at least some of the time (for example at a point in time during its replication cycle).

Preferably, said DNA constructs which are capable of episomal replication are present in the host cell in a copy number of at least 1, preferably at least 5, especially preferably at least 10.

"Selection of prokaryotic host cells comprising said DNA construct in episomal form" means choosing host cells comprising said DNA construct in episomal form. They can be chosen for example using a selection marker described hereinbelow. Preferably, the DNA construct does not insert into the chromosomal DNA of the host cell. This can be prevented for example by the DNA construct lacking sequences which are identical with chromosomal sequences of the host cell over a substantial section.

Preferably, said DNA constructs which are capable of episomal replication have a size/length of no more than 100 000 bases or base pairs, especially preferably no more than 50 000 bases or base pairs, very especially preferably 10 000 bases or base pairs (the number of bases or base pairs depends on whether the DNA construct is a single- or double-stranded DNA structure).

The DNA construct is preferably a vector. By way of example, vectors can be plasmids, cosmids, phages, viruses, retroviruses or else *agrobacteria*. The vector is preferably a circular plasmid which comprises the nucleic acid sequence to be expressed in recombinant form and capable of autonomously replicating in the prokaryotic host cell. Within the scope of the present invention, vector can also be referred to as recombinant vector or recombinant expression vector. The skilled worker is familiar with various sequences which permit the replication of DNA in prokaryotes. Examples which may be mentioned are OR1 (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

Correspondingly suitable replication origins which ensure a low copy number can be isolated from BACs (bacterial artificial chromosomes), F-plasmids, cosmids such as, for example, pWE15.

Correspondingly suitable replication origins which ensure a medium copy number can be isolated for example from pBR322 (Lin-Chao S, Bremer H, Mol Gen Genet 1986 203 (1): 143-149) and derivatives such as the pJOE series, pKK223-3, pQE30, pQE40 or plasmids with an R1 origin such as pRSF1010 and derivatives such as, for example, pML122, p15A, pSC101. Correspondingly suitable replication origins which ensure a high copy number can be isolated for example from phagemids such as pBluescript II SK/KS+/−, PGEM etc. The copy number which is present in a cell in each case is determined in part by what is known as the replication origin (also referred to as replicon). Plasmids of the pBR322 series comprise the ColE1 replication origin from pMB1. This replication origin is relatively tightly regulated and results in a copy number of approximately 25 per cell. pUC plasmids comprise a mutated ColE1 version and can be present as 200 to 700 plasmid copies per cell. Some plasmids comprise the p15A replication origin, which results in a low copy number.

Examples of vectors which may be mentioned:
a) the following are preferred in *E. coli*: pQE70, pQE60 and pQE-9 (QIAGEN, Inc.); pBluescript vectors, Phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.); pLG338, pACYC184, pBR322, pUC18, pUC19, pKC30, pRep4, pHS1, pHS2, pPLc236, pMBL24, pLG200, pUR290, pIN-III$^{113}$-B1, λgt11 or pBdCI,
b) the following are preferred in *Streptomyces*: pIJ101, pIJ364, pIJ702 or pIJ361,
c) the following are preferred in *Bacillus*: pUB110, pC194 or pBD214,
d) in *Corynebacterium*: pSA77 or pAJ667,
or derivatives of the abovementioned plasmids. The plasmids mentioned are a small selection of the plasmids which are possible. Further plasmids are well known to the skilled worker and can be found for example in the book Cloning Vektors (Eds. Pouwels P. H. et al. Elsevier, Amsterdam-New York-Oxford, 1985, ISBN 0 444 904018).

"Transformation" or "transformed" means the introduction of genetic material such as, for example, a vector (for example a plasmid) into a prokaryotic host cell. The skilled worker has available for this purpose a variety of methods described in detail hereinbelow. A prokaryotic host cell into which said genetic material has been introduced, and also the "progeny" and colonies resulting from this cell and which comprise said genetic material are referred as to "transformants".

"Transduction" or "transduced" means the introduction of genetic material into a prokaryotic host cell starting from the genetic material of a bacteriophage. A prokaryotic host cell into which said genetic material has been introduced, and also the "progeny" and colonies resulting from this cell and which comprise said genetic material are referred as to "transductants".

"Recombinant protein" means any protein product which, starting from the nucleic acid sequence to be expressed, can be expressed under the functional control of the L-rhamnose-inducible promoter and includes peptides, polypeptides, proteins, oligoproteins and/or fusion proteins. "Recombinant protein" preferably means a protein of microbial, bacterial, animal or vegetable origin.

"Fusion proteins" means a fusion of the desired protein and leader sequences which make possible an expression in specific compartments (for example periplasm or cytoplasm) of the host cell or into the surrounding medium. An example which may be mentioned is the pelB leader sequence (U.S. Pat. No. 5,576,195; U.S. Pat. No. 5,846,818).

"Expression cassette" means in each case the combination of a promoter with at least one nucleic acid sequence which can be transcribed under the control of the former.

"Heterologous" with regard to the ratio of the L-rhamnose-inducible promoter and the nucleic acid sequence to be expressed under the control of said promoter, or an expression cassette or an expression vector, means all those constructs which have been generated by recombinant methods in which either
a) at least one of the nucleic acid sequences to be expressed, or
b) at least one of the L-rhamnose-inducible promoters which controls the expression of said nucleic acid sequence to be expressed, or
c) (a) and (b)
are not in their natural genetic environment (for example at their natural chromosomal locus) or have been modified by recombinant methods, it being possible for the modification to comprise, for example, substitutions, additions, deletions, inversions or insertions of one or more nucleotide residues.

In the method according to the invention, the prokaryotic host cells according to the invention are grown in a medium which permits the growth of these organisms. This medium may be a synthetic or a natural medium. Depending on the organism, media known to the skilled worker are used. To allow microbial growth, the media used comprise a carbon source, a nitrogen source, inorganic salts and, if appropriate, minor amounts of vitamins and trace elements.

Advantageous carbon sources are, for example, polyols such as glycerol, sugars such as mono-, di- or polysaccharides such as glucose, fructose, mannose, xylose, galactose, ribose, sorbose, ribulose, lactose, maltose, sucrose, raffinose, starch or cellulose, complex sugar sources such as molasses, sugar phosphates such as fructose-1,6-bisphosphate, sugar alcohols such as mannitol, alcohols such as methanol or ethanol, carboxylic acids such as citric acid, lactic acid or acetic acid, fats such as soya oil or rapeseed oil, amino acids such as a mixture of amino acids, for example so-called casamino acids (Difco), or individual amino acids such as glycine or aspartic acid or amino sugars which may simultaneously also be used as the nitrogen source. Especially preferred are polyols, in particular glycerol.

The medium employed as basal medium should preferably not comprise L-rhamnose to ensure the tightest possible expressional regulation. If required, L-rhamnose is then added at the desired point in time or cell density and in the concentration desired in each case.

Advantageous nitrogen sources are organic or inorganic nitrogen compounds or materials which comprise these compounds. Examples are ammonium salts such as $NH_4Cl$ or $(NH_4)_2SO_4$, nitrates, urea or complex nitrogen sources such as cornsteep liquor, brewer's yeast autolyzate, soybean flour, wheat gluten, yeast extract, meat extract, casein hydrolyzate, yeast or potato protein, all of which can frequently also act as the nitrogen source.

Examples of inorganic salts are the salts of calcium, magnesium, sodium, cobalt, molybdenum, manganese, potassium, zinc, copper and iron. Anions of these salts to be mentioned are, in particular, the chloride, sulfate and phosphate ion. An important factor for increasing the productivity in the method according to the invention is the control of the $Fe^{2+}$- or $Fe^{3+}$ ion concentration in the production medium.

If appropriate, other growth factors are added to the nutrient medium, such as, for example, vitamins or growth promoters such as biotin, 2-KLG, thiamin, folic acid, nicotinic acid, pantothenate or pyridoxin, amino acids such as alanine, cysteine, proline, aspartic acid, glutamine, serine, phenylalanine, ornithine or valine, carboxylic acids such as citric acid, formic acid, pimelic acid or lactic acid, or substances such as dithiothreitol.

The mixing ratio of said nutrients depends on the type of fermentation and is decided for each individual case. All of the components of the medium may be introduced into the fermentation vessel at the beginning of the fermentation, if appropriate after having been sterilized separately or jointly, or else they may be fed continuously or batchwise during the fermentation, as required.

The culture conditions are specified in such a way that the organisms' growth is optimal and that the best possible yields are achieved (this can be determined for example on the basis of the activity level of the recombinant protein expressed).

Preferred culture temperatures are at 15° C. to 40° C. Temperatures between 25° C. and 37° C. are especially advantageous. The pH is preferably maintained in a range of from 3 to 9. pH values of between 5 and 8 are especially advantagous. In general, an incubation time of a few hours to several days, preferably 8 hours up to 21 days, especially preferably 4 hours to 14 days, will suffice. The maximum amount of product accumulates in the medium within this period.

Advantageous media optimization can be found by the skilled worker for example in the textbook Applied Microbiol. Physiology, "A Practical Approach (Eds. P M Rhodes, P F Stanbury, IRL-Press, 1997, pages 53-73, ISBN 0 19 963577 3).

The method according to the invention can be carried out continuously or discontinuously, batchwise or fed-batchwise.

"Mutation" or "mutations" means the substitution, addition, deletion, inversion or insertion of one or more amino acid residue(s) or base(s)/base pair(s).

"Homology" between two nucleic acid sequences means the identity of the nucleic acid sequence over in each case the sequence length indicated, which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389ff), setting the following parameters:

| Gap Weight: 50 | Length Weight: 3 |
| Average Match: 10 | Average Mismatch: 0 |

For example, a sequence with at least 50% homology with the sequence SEQ ID NO: 2 at the nucleic acid level is understood as meaning a sequence which, upon alignment with the sequence SEQ ID NO: 2 using the above program algorithm with the above parameter set has at least 50% homology.

"Homology" between two polypeptides means the identity of the amino acid sequence over in each case the sequence length indicated, which is calculated by comparison with the aid of the program algorithm GAP (Wisconsin Package Version 10.0, University of Wisconsin, Genetics Computer Group (GCG), Madison, USA), setting the following parameters:

| Gap Weight: 8 | Length Weight: 2 |
| Average Match: 2912 | Average Mismatch: −2003 |

For example, a sequence with at least 50% homology with the sequence SEQ ID NO: 9 at the protein level is understood as meaning a sequence which, upon alignment with the sequence SEQ ID NO: 9 using the above program algorithm with the above parameter set has at least 50% homology.

For optimal expression of heterologous genes in organisms, it may be advantageous to modify the nucleic acid sequences in accordance with the specific codon usage of the organism. The codon usage can easily be established on the basis of computer analyses of other, known genes of the organism in question.

The DNA construct which comprises the L-rhamnose-inducible promoter and the nucleic acid sequence to be expressed under its control ensures the transcription and/or translation of said nucleic acid sequence as the result of a functional linkage of said promoter and said nucleic acid sequence.

A functional linkage is generally understood as meaning an arrangement in which a genetic control sequence can exert its function with regard to the nucleic acid sequence to be expressed. In this context, function can mean, for example, expressional control, i.e. transcription and/or translation of the nucleic acid sequence. In this context, control comprises for example the initiation, enhancement, control or suppression of expression, i.e. transcription and, if appropriate, translation. A functional linkage is understood as meaning, for example, the sequential arrangement of a promoter, the nucleic acid sequence to be expressed and, if appropriate, further regulatory elements such as, for example, a terminator, in such a way that each of the regulatory elements can fulfill its function when the nucleic acid sequence is expressed. The skilled worker is familiar with various ways of arriving at one of the DNA constructs according to the invention. The construction can be carried out by means of customary recombination and cloning techniques as are described, for example, in T Maniatis, E F Fritsch and J Sambrook, Molecular Cloning: A Laboratory Manual, Cold Spring Harbor Laboratory, Cold Spring Harbor, N.Y. (1989) and in T J Silhavy, M L Berman and L W Enquist, Experiments with Gene Fusions, Cold Spring Harbor Laboratory, Cold Spring Harbor, N.Y. (1984) and in Ausubel, F M et al., Current Protocols in Molecular Biology, Greene Publishing Assoc. and Wiley Interscience (1987).

Said DNA construct can comprise further functional elements. The concept of the functional elements is to be interpreted broadly and means all those sequences which have an effect on the production, the multiplication or the function of the DNA constructs or organisms according to the invention. Functional elements ensure, enhance, regulate or modify for example the transcription and, if appropriate, translation in corresponding host organisms.

Function elements are described for example in "Goeddel; Gene Expression Technology: Methods in Enzymology 185, Academic Press, San Diego, Calif. (1990)" or "Gruber and Crosby, in: Methods in Plant Molecular Biology and Biotechnolgy, CRC Press, Boca Raton, Fla., eds.: Glick and Thompson, Chapter 7, 89-108" and the references cited therein. Depending on the host organism or starting organism described hereinbelow in greater detail, which is converted into a genetically modified or transgenic organism by introducing the expression cassettes or vectors, different control sequences are suitable.

"Genetic control sequences" comprise for example the 5'-untranslated region or the noncoding 3' region of genes. "Genetic control sequences" furthermore mean sequences which encode fusion proteins consisting of a signal peptide sequence. The following may be mentioned by way of example but not by limitation:

a) Selection Markers

As a rule, selection markers are necessary for selecting successfully transformed cells and preventing the loss of the DNA construct from the host cell in the course of time and while cell division takes place. Such a loss can occur in particular when the recombinant protein encoded by the nucleic acid sequence to be expressed has a toxic effect on the prokaryotic organism. The selectable marker which is introduced together with the expression construct confers a resistance to a biocide (for example an antibiotic such as, for example, ampicillin, kanamycin or hygromycin) to the successfully transformed cells. Examples of selection markers which may be mentioned are:

Amp (ampicillin resistance; β-lactamase)
Cab (carbenicillin resistance)
Cam (chloramphenicol resistance)
Kan (kanamycin resistance)
Rif (rifampicin resistance)
Tet (tetracyclin resistance)
Zeo (zeocin resistance)
Spec (spectinomycin)

The selection pressure is maintained by suitable amounts of the antibiotic. Examples which may be mentioned are: ampicillin 100 mg/l, carbenicillin 100 mg/l, chloramphenicol 35 mg/l, kanamycin 30 mg/l, rifampicin 200 mg/l, tetracyclin 12.5 mg/l, spectinomycin 50 mg/l.

Selection markers furthermore comprise those genes and gene products which make possible a selection of a suitably transformed host cell, for example by complementing a genetic deficiency in amino acid or nucleotide synthesis. Generally, media which do not comprise said amino acid or nucleotide unit are employed for this purpose. The skilled worker is familiar with a variety of such systems. Examples which may be mentioned are the deficiencies in the biosynthesis of tryptophan (for example trpC), leucine (for example leuB), histidine (for example hisB) as they are present, for example, in E. coli strain KC8 (Clontech). These deficiencies can be complemented, inter alia, by the selectable markers TRP1, Leu2 and HIS3.

b) Transcription terminators

The transcription terminator reduces unwanted transcription and increases the plasmid and mRNA stability.

c) Shine-Dalgarno sequences

A Shine-Dalgarno (SD) sequence is required for initiating translation and is complementary to the 3' end of the 16S ribosomal RNA. The efficiency of initiating translation at the start codon depends on the actual sequence. A suitable consensus sequence for E. coli is, for example, 5'-TAAGGAGG-3'. It is located approximately 4 to 14 nucleotides upstream of the start codon, the optimum being 8 nucleotides. To avoid the formation of secondary structures (which may reduce expression), this region should preferably be rich in A/T nucleotides.

d) Start codon

The start codon is the point at which translation is initiated. In E. coli, ATG is the most widely used start codon; as an alternative GTG may also be used.

e) "Tags" and Fusion Proteins

N- or C-terminal fusions between recombinant proteins to be expressed and shorter peptides ("tags") or other proteins (fusion partners) may be advantageous. For example, they may make possible an improved expression, solubility, detectability and purification. Preferably, such fusions are combined with protease cleavage sequences (for example for thrombin or factor X), which make possible a removal of the "tag" or the fusion partner after expression and purification has taken place.

f) Multiple Cloning Regions (Multiple Cloning Sites; MCS) Permit and Facilitate the Insertion of One or More Nucleic Acid Sequences.

g) Stop Codon/Translation Terminators

Of the three possible stop codons, TAA is preferred since TAG and TGA can, under some circumstances, result in a read-through without terminating the translation. To ensure reliable termination, it is also possible to employ a plurality of stop codons in sequence.

h) Reporter Genes

Reporter genes encode readily quantifiable proteins which ensure an assessment of the transformation efficiency, the expression level and the place or time of expression via their intrinsic color or enzyme activity. Reporter genes can, for example, encode the following proteins: hydrolases, fluorescence proteins, bioluminescence proteins, glucosidases or peroxidases. Preferred are luciferases, β-galactosidases, β-glucuronidase, green fluorescence protein, acetyltransferases, phosphotransferases or adenyltransferases (see also Schenborn E, Groskreutz D (1999) Mol Biotechnol 13(1):29-44).

In the case of selection markers or reporter proteins, the nucleic acid sequence encoding said proteins is preferably linked functionally with a promoter which is functional in the prokaryotic host organism in question and, if appropriate, further control sequences to give an expression cassette. Advantageous promoters and control sequences are generally known to the skilled worker. Examples which may be mentioned are promoters such as the cos, tac, trp, tet, lpp, lac, laciq, T7, T5, T3, gal, trc, ara, SP6, λ-PR or λ-PL promoter.

The production of a transformed host cell or a transformed host organism requires introduction of the DNA in question (for example one of the expression cassettes or vectors according to the invention) into the host cell in question. A large number of methods is available for this process, which is referred to as transformation (see also Keown et al. (1990) Methods in Enzymology 185:527-537). Thus, the DNA can be introduced for example directly by means of microinjection, electroporation or by bombardment with DNA-coated microparticles (biolistic methods with the gene gun; particle bombardment). Also, the cell can be permeabilized chemically, for example with polyethylene glycol, so that the DNA can enter the cell by diffusion. The DNA can also take place by means of fusion with other DNA-comprising units such as minicells, cells, lysosomes or liposomes. Electroporation is another suitable method for introducing DNA, in which the cells are reversibly permeabilized by an electrical pulse. Preferred general methods which may be mentioned are calcium-phosphate-mediated transformation, DEAE-dextran-mediated transformation, cationic lipid-mediated transformation, electroporation, transduction, infection. Such methods are known to the skilled worker and described by way of example (Davis et al. (1986) Basic Methods In Molecular Biology; Sambrook J et al. (1989) Molecular cloning: A laboratory manual, Cold Spring Harbor Laboratory Press; Ausubel F M et al. (1994) Current protocols in molecular biology, John Wiley and Sons; Glover D M et al. (1995) DNA Cloning Vol. 1, IRL Press ISBN 019-963476-9).

Transformed cells, i.e. those which comprise the DNA which has been introduced, can be selected from untransformed cells when a selectable marker is part of the DNA which has been introduced. Various selection markers are described above.

The method according to the invention is not limited regarding the nature and sequence of the nucleic acid sequence to be expressed, or of the recombinant protein expressed on the basis thereof. The nucleic acid sequences to be expressed under the control of the L-rhamnose-inducible promoter can be diverse. In this context, expression means transcription and, if appropriate, translation. Besides the expression of nucleic acid sequences which encode recombinant proteins, it is also possible to express nucleic acid sequences which, for example, bring about the transcription of an antisense RNA and thus reduce the expression of an endogenous gene of the prokaryotic host cell. It is possible to express sequences of prokaryotic, but also of eukaryotic origin. It is preferred to express sequences which encode recombinant proteins which are to be produced in substantial quantities. The following may be mentioned by way of example, but not by limitation:

a) enzymes such as, for example, chymosin, proteases, polymerases, saccharidases, dehydrogenases, nucleases, glucanases, glucose oxidase, α-amylase, oxidoreductases (such as peroxidases or laccases), xylanases, phytases, cellulases, collagenases, hemicellulases and lipases. Especially preferred are enzymes as are used in laundry detergents or other detergents such as, for example, horseradish peroxidase, proteases, amylases, lipases, esterases or cellulases enzymes as are used in the food industry such as proteases, lipases, lactases, β-glucanase, cellulases or pectinases enzymes as are employed in industrial processes such as lipases, α-amylases, amyloglucosidases, glucoamylases, pullulanases, glucose isomerases, enzymes as are employed in industrial processes for the production of chemicals and fine chemicals such as lipases, amidases, nitrile hydratases, esterases or nitrilases enzymes as are employed in animal nutrition such as β-glucanases enzymes as are employed in papermaking or in the leather industry such as amylases, collagenases, cellulases or xylanases.

b) mammalian proteins such as, for example, blood proteins (for example serum albumin, factor VII, factor VIII, factor IX, factor X, tissue plasminogen factor, protein C, von Willebrand factor, anti-thrombin 111 or erythropoietin), colony stimulating factors (CFS) (for example granulocyte colony-stimulating factor (G-CSF), macrophage colony-stimulating factor (M-CSF) or granulocyte macrophage colony-stimulating factor (GM-CSF)), cytokins (for example interleukins), integrins, addressins, selectins, antibodies or antibody fragments, structural proteins (for example collagen, fibroin, elastin, tubulin, actin or myosin), growth factors, cell-cycle proteins, vaccines, fibrinogen, thrombin, insulins.

The nucleic acid sequence to be expressed especially preferably encodes a recombinant protein selected from the group consisting of chymosines, proteases, polymerasen, saccharidases, dehydrogenases, nucleases, glucanases, glucose oxidases, α-amylases, oxidoreductases, peroxidases, laccases, xylanases, phytases, cellulases, collagenases, hemicellulases, lipases, lactases, pectinases, amyloglucosidases, glucoamylases, pullulanases, glucose isomerases, nitrilases, esterases, nitrile hydratases, amidases, oxygenases, oxynitrilases, lyases, lactonases, carboxylases, collagenases, cellulases, serum albumins, factor VII, factor VIII, factor IX, factor X, tissue plasminogen factors, protein C, von Willebrand factors, antithrombins, erythropoietins, colony-stimulating factors, cytokins, interleukins, insulins, integrins, addressins, selectins, antibodies, antibody fragments, structural proteins, collagen, fibroins, elastins, tubulins, actins, myosins, growth factors, cell-cycle proteins, vaccines, fibrinogens and thrombins.

In a preferred embodiment, the recombinant protein is a nitriliase, preferably a nitrilase described by an amino acid sequence which is encoded by a nucleic acid sequence selected from the group consisting of a) a nucleic acid sequence with the sequence shown in SEQ ID NO: 6, b) nucleic acid sequences which, owing to the degeneracy of the genetic code, are derived from the nucleic acid sequence shown in SEQ ID NO: 6, c) derivatives of the nucleic acid sequence shown in SEQ ID NO: 6 which encode polypeptides with the amino acid sequences shown in SEQ ID NO: 7 and which have at least 35% homology at the amino acid level without the enzymatic activity of the polypeptides being substantially reduced.

A further aspect of the invention relates to the use of the above-described host cells or host organisms according to the invention for the production of foodstuffs, feedstuffs, pharmaceuticals or fine chemicals. Fine chemicals preferably means proteins, enzymes, vitamins, amino acids, sugars, fatty acids, natural and synthetic flavorings, aroma chemicals and colorants.

The invention furthermore relates to methods for the production of recombinant proteins, enzymes and other fine chemicals such as, for example, aldehydes, ketones or carboxylic acids (preferably chiral carboxylic acids) using one of the prokaryotic host cells according to the invention or a preparations thereof. The preferred proteins and enzymes are detailed hereinabove.

In this context, the prokaryotic host cell can be present in a growing, quiescent, immobilized or disrupted state. Disrupted cells are understood as meaning, for example, cells which have been made permeable via treatment with, for example, solvents, or cells which have been disrupted via an enzymatic treatment, a mechanical treatment (for example French press or sonication) or via any other method. The resultant crude extracts are advantageously suitable for the method according to the invention. Partially purified enzyme preparations may also be used for the method. Immobilized microorganisms or enzymes which can advantageously be used in the reaction are likewise suitable.

A further aspect of the invention relates to methods for the production of chiral carboxylic acids, where a racemic nitrile (or, as an alternative, its precursors aldehyde and hydrocyanic acid/cyanide salt) is converted into said chiral carboxylic acid by treatment with a prokaryotic host cell which is at least deficient with regard to one L-rhamnose isomerase and comprises at least one DNA construct which can replicate in said host cell and which comprises a nucleic acid sequence encoding a nitrilase under the transcriptional control of an L-rhamnose-inducible promoter, where said promoter is heterologous with regard to said nucleic acid sequence.

The nucleic acid sequence which encodes the nitrilase is preferably selected from the group of the above-shown sequences which encode nitrilases.

Chiral carboxylic acids are sought-after compounds for organic synthetic chemistry. They are starting materials for a multiplicity of pharmaceutical active ingredients or active ingredients for crop protection. Chiral carboxylic acids can be used for traditional racemate resolution via diastereomer salts. Thus, for example, R-(−)- or S-(−)-mandelic acid is employed for the racemate resolution of racemic amines. R-(−)-Mandelic acid is furthermore used as intermediate for synthesis purposes.

In a preferred embodiment, the chiral carboxylic acids of the general formula I are prepared starting from a racemic nitrile of the general formula II.

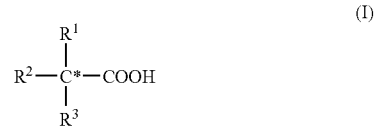

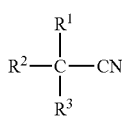

(II)

where
* is an optically active center
$R^1$, $R^2$, $R^3$ are independently of one another hydrogen, substituted or unsubstituted, branched or unbranched C1-C10-alkyl-, C2-C10-alkenyl-, substituted or unsubstituted aryl-, hetaryl-, $OR^4$ or $NR^4R^5$ and where the radicals $R^1$, $R^2$ and $R^3$ are always different,
$R^4$ is hydrogen, substituted or unsubstituted, branched or unbranched C1-C10-alkyl-, C2-C10-alkenyl-, C1-C10-alkylcarbonyl-, C2-C10-alkenylcarbonyl-, aryl-, arylcarbonyl-, hetaryl- or hetarylcarbonyl-,
$R^5$ is hydrogen, substituted or unsubstituted, branched or unbranched C1-C10-alkyl-, C2-C10-alkenyl-, aryl- or hetaryl-.

Most preferred as the nitrile are mandelonitrile, o-chloromandelonitrile, p-chloromandelonitrile or m-chloromandelonitrile. Most preferred as the chiral carboxylic acid are R-mandelic acid, S-mandelic acid, R-p-chloromandelic acid, S-p-chloromandelic acid, R-m-chloromandelic acid, S-m-chloromandelic acid, R-o-chloromandelic acid or S-o-chloromandelic acid.

Details for carrying out these conversions or for purifying the products and the like are described in detail for example in WO 00/23577. The starting materials, products and process parameters described therein are expressly referred to.

EXAMPLES

General nucleic acid methods such as, for example, cloning, restriction cleavages, agarose gel electrophoresis, linking DNA fragments, transformation of microorganisms, bacterial cultures and sequence analysis of recombinant DNA were carried out as described by Sambrook et al. (1989) (Cold Spring Harbor Laboratory Press: ISBN 0-87969-309-6), unless otherwise specified. Recombinant DNA molecules were sequenced with an ABI laser fluorescence DNA sequencer following the method of Sanger (Sanger et al. (1977) Proc Natl Acad Sci USA 74:5463-5467). To avoid polymerase errors in constructs to be expressed, fragments resulting from a polymerase chain reaction were sequenced and verified.

EXAMPLES 1

Characterization of the E. coli strain JB1204

In accordance with the literature, Escherichia coli JB1204 (CGSC6999, Bulawa C E & Raetz C R H (1984) J Biol Chem 259:11257-11264) has a transposon insertion "rha-14::Tn10", no more detailed information being given of the sequence or function of "rha-14". JB1204 (a K12 derivative) is inferior to strains such as TG1 and W3110 with regard to growth, as the result of a number of other mutations, which is why this strain itself is not used for the production of proteins on an industrial scale.

To test if the strain E. coli JB1204 still metabolizes rhamnose and if the induction of a rhamnose-dependent expression system in E. coli JB1204 is adversely affected, competent JB1204 cells were prepared and transformed with the plasmid pDHE1650, which is a pJOE derivative and carries the gene for a nitrilase under the control of the rhamnose promoter (plasmid corresponds to pDHE19.2 in DE 19848129). After 15 hours of culture at 37° C. in LB-ampicillin-tetracyclin with and without rhamnose, the optical density of the cultures was measured and, after the cells had been washed, the nitrilase activity was tested in what is known as the resting-cell assay (see Table 1). When grown in the presence of L-rhamnose, nitrilase expression takes place in JB1204 and in the comparison strain TG1, but this expression does not take place in the absence of L-rhamnose.

TABLE 1

| Sample | Rhamnose supplementation [g/L] | Rhamnose consumption | $OD_{600}$ | Mandelonitrile conversion |
|---|---|---|---|---|
| 1 | 2 | − | 5.9 | + |
| 1 | 0 | − | 5.7 | − |
| 2 | 2 | + | 11.9 | + |
| 2 | 0 | − | 8.0 | − |

1, E. coli JB1204 pDHE1650 in LB Amp Tet;
2, E. coli TG1 pDHE1650 in LB Amp (positive control)

Assay conditions: 10 mM Tris-HCl, 6 mM mandelonitrile, 40° C.
Analysis: Stop sample with 40 µl of 1M HCl/ml, remove cells and then analyze by HPLC as described in DE 19848129.

EXAMPLE 2

Preparation of the Rhamnose-Deficient Host Strain TG10 for the Production of Recombinant Proteins The strain TG1, which is utilized for the production of recombinant biocatalysts, was modified by P1 transduction in such a way that it no longer metabolizes rhamnose, while the rhamnose-induction-based expression system of the pJOE and pDHE vectors continues to function without being adversely affected (name of this new strain derivative: TG10).

The choice of the E. coli strain is important for being able to conduct fermentative methods in an inexpensive manner and in high yields. This is why E. coli TG1, which is known for productive high-density cell fermentations (Korz et al. (1995) J Biotechnol 39:59-65) was chosen as the host strain. The rhamnose deficiency from JB1204 was transferred to TG1 pDHE1650 by P1 transduction and selection on 15 µg/ml tetracyclin (=TG10 pDHE1650=Lu10569).

2.1 P1 transduction protocol for transferring the rhamnose deficiency from JB1204 (rha14::Tn10) to TG1
a) Preparation of the Donor Lysate
Grow the donor, i.e. JB1204, in 3 ml LB-Tet (15 µg/ml) for 15 hours at 37° C. (preculture).
Incubate 3 ml LB-Tet+5 mM $CaCl_2$+60 µl preculture (=1:50) up to OD600=0.3-0.5 at 37° C. (approx. 45 minutes)
+100 µl (fresh) lysate of phage P1, continue shaking thoroughly for 10-120 minutes until cell lysis takes place (clarification, up to 5 hours for old lysate)
+60 µl chloroform, vortex for 30 seconds to destroy residual cells, storage at 4° C.
b) Infection of the Recipient
Grow the recipient, i.e. TG1 pDHE1650 (=Lu9682) in 3 ml LB-Amp for approx. 15 hours at 37° C. (preculture)
Incubate 5 ml LB-Amp+5 mM $CaCl_2$+10 mM $MgCl_2$+10 mM $MgSO_4$+100 µl preculture (=1:50) up to OD600=0.3-0.5 at 37° C. (approx. 30 minutes), remaining preculture on ice
Harvest preculture and main culture, resuspend in 2.5 ml of LB-Amp-Ca-Mg
Treat in each case 2×100 µl of recipient with 0, 5, 30, 100 µl of donor lysate and incubate together with a control without recipient +100 µl of donor lysate for 8 minutes and 24 minutes, respectively, without shaking at 30° C. (infection)

+100 µl 1M sodium citrate pH 7.0, centrifuge for 2 minutes at 7000 rpm, wash 2-3× in 1 ml of 0.1M citrat buffer pH 7.0 and resuspend, 1 hour 37° C., without shaking Harvest, resuspend in 100 µl 0.02 M sodium citrate pH 7.0

Plate in each case 80 µl on LB-Amp-Tet and in each case 10 µl of the mixtures without donor lysate addition on LB-Amp, incubation overnight at 37° C.

LB-Amp gives rise to a lawn (control). Pick colonies from LB-Amp-Tet and verify resistances, rhamnose deficiency, rhamnose inducibility and activity.

Also, TG1 pDHE1650 pAgro4 pHSG575, the equivalent to TG1 pDHE1650 with chaperone coexpression (GroESL), was transduced in parallel (+spectinomycin 50 µg/ml and chloramphenicol 10 µg/ml in the medium; name TG10 pDHE1650 pAgro4 pHSG575=Lu10571).

After the clones obtained were cultured overnight in 3 ml of LB/ampicillin/rhamnose (approx. 2 g/l) medium (+tetracyclin 10 µg/ml), the optical densities (λ=600 nm) of the cultures were determined. HPLC analysis of the culture supernatants revealed that the resulting *E. coli* strain TG10 pDHE1650 cannot metabolize rhamnose. The cells were subsequently washed in buffer and assayed for their nitrilase activity in a resting-cell-assay (Table 2).

The rhamnose deficient clones showed a similar nitrile hydrolyzing activity to the corresponding comparison strain (TG1pDHE1650). The rhamnose concentration hardly decreased in the clones.

pDHE1650). To this end, *E. coli* TG10 pDHE1650 was inoculated from ice into 3 ml of LB-Tet without ampicillin and incubated overnight at 37° C. This culture was used to inoculate a 3 ml main culture 1:100 in LB-Tet, which was subjected to a heat shock treatment (2.5 minutes, 42° C.). After shaking for 16 hours at 37° C., the $OD_{600}$ of the culture was 1.3 (corresponds to approx. $1.3 \times 10^9$ cells/ml). In each case 100 µl of the dilution steps $10^{-4}$ to $10^{-7}$ were plated onto LB-Tet, and the resulting colonies (560+140+15+0) were transferred to LB-Tet with ampicillin by the replica method. A clone which showed weak growth on this medium was again plated onto LB-Amp-Tet. It neither grew on LB-Amp-Tet nor did it show any plasmid DNA following minipreparation (LB-Tet culture). This ampicillin-sensitive clone is named TG10 (=Lu10568) and is used as starting strain for new overexpression strains.

EXAMPLE 4

Production of Recombinant L-Pantolactone Hydrolase Using the Rhamnose-Deficient Host Strain *E. coli* TG10

Competent *E. coli* TG10 cells were prepared and transformed with the plasmids pDHE681, pAgro4 and pHSG575

TABLE 2

| Sample | Remaining rhamnose [g/L] | Cell conc. [times x] | Incub. time [mins] | Acid [mM] | Activity (1x) [U/L] | $OD_{600}$ | Activity/ $OD_{600}$ MW [U/L] |
|---|---|---|---|---|---|---|---|
| Blank | — | 0 | 60 | 0.01 | 0 | | |
| TG10 pDHE1650 | 1.71 | 0.01 | 60 | 1.02 | 1700 | 6.01 | 324 |
| | | 0.05 | 10 | 1.10 | 2200 | | |
| TG1 pDHE1650 | 0 | 0.01 | 60 | 0.84 | 1400 | 7.90 | 180 |
| | | 0.05 | 10 | 0.72 | 1440 | | |
| TG10 pDHE1650 pAgropHSG | 1.67 | 0.01 | 60 | 0.78 | 1300 | 5.01 | 295 |
| | | 0.05 | 10 | 0.83 | 1660 | | |
| TG1 pDHE1650 pAgropHSG | 0.34 | 0.01 | 60 | 1.18 | 1967 | 7.51 | 297 |
| | | 0.05 | 10 | 1.25 | 2500 | | |

Assay conditions: 10 mM Tris-HCl, 6 mM mandelonitrile, 40° C.
Analysis: stop sample with 40 µl of 1M HCl/ml, remove cells and then analyze by HPLC as described in DE 19848129 (1U = 1 µmol mandelic acid/min)

EXAMPLE 3

Curing of the Rhamnose-Deficient Host Strain TG10 pDHE1650

The transduction with *E. coli* TG1 pDHE1650 had the advantage of selecting against the original strain JB1204 with ampicillin. However, subsequent work required a plasmid-free host strain, i.e. the plasmid pDHE1650 was to be removed from TG10 pDHE1650 (curing of TG10

(=sample 1 in Table 3). After overnight culture at 37° C., the cells showed a high L-pantolactone-hydrolyzing activity in comparison with the control strain in question (TG1 pDHE681 pAgro4 pHSG575=sample 2 in Table 3), whose maximum activity is, as a rule, reached after incubation for 6-7 hours (approx. 1500 U/L) and drops drastically upon longer incubation. The rhamnose (0.5 g/L) was not metabolized by TG10 pDHE681 pAgro4 pHSG575.

TABLE 3

| Sample | Remaining rhamnose [g/L] | $OD_{600}$ | Cell conc. [times x] | Incub. time [h] | Acid [mM] | Activity (1x) [U/L] | Activity/ $OD_{600}$ [U/L] |
|---|---|---|---|---|---|---|---|
| Blank | — | | | 0 | 1.0 | 1.74 | — |
| 1 | 0.52 | 6.35 | 0.2 | 1.0 | 29.9 | 2344.2 | 369.2 |
| 2 | 0 | 6.64 | 0.2 | 1.0 | 6.27 | 377.5 | 56.9 |

1, TG10 pDHE681 pAgro4 pHSG575; LB with ampicillin (Amp; 100 µg/ml) tetracyclin (Tet 10 µg/ml), L-rhamnose (Rha 0.5 g/l) and isopropyl thiogalactoside (IPTG 0.15 mM)
2, TG1 pDHE681 pAgro4 pHSG575; LB with ampicillin (Amp; 100 µg/ml), L-rhamnose (Rha 0.5 g/l) and isopropyl thiogalactoside (IPTG 0.15 mM)

The assay was repeated in greater detail. The addition of tetracyclin (15 μg/ml) to the medium is not necessary for maintaining the rhamnose deficiency.

EXAMPLE 5

Determining the Dependency of the Induction on the L-Rhamnose Concentration

The strain *E. coli* TG10 (pDHE1650, pAgro4, pHSG575) was grown analogously to Example 1 on LB ampicillin (100 mg/l), chloramphenicol 10 mg/l, spectinomycin (50 mg/l), IPTG 0.15 mM in the presence of various rhamnose concentrations (0 to 2 g/l rhamnose) and analyzed (in duplicate) for its specific nitrilase activity. A concentration of as little as 0.01 g/l L-rhamnose results in, on average, a significant induction of expression, while no significant expression was determined (via the enzyme activity) in the absence of rhamnose.
cf. also FIG. 1:
A: Diagram of the relative activity (Rel. Act. %) as a function of the L-rhamnose concentration (Conc. in g/l)
B: Diagram of the relative specific activity (Rel. Spec. Act. %) as a function of the L-rhamnose concentration (Conc. in g/l)

TABLE 4

| Rhamnose conc. | OD600 | Rel. Activ. | Rel. spec. Act. [g/l] |
|---|---|---|---|
| 0.00 | 5.4 | 0.1% | 0.1% |
| 0.01 | 6.2 | 66% | 65% |
| 0.02 | 5.8 | 70% | 73% |
| 0.04 | 5.7 | 85% | 92% |
| 0.05 | 5.2 | 83% | 98% |
| 0.07 | 5.9 | 90% | 93% |
| 0.10 | 6.0 | 97% | 98% |
| 0.15 | 5.6 | 101% | 111% |
| 0.20 | 5.6 | 100% | 108% |
| 0.30 | 5.3 | 99% | 115% |
| 0.40 | 5.7 | 107% | 114% |
| 0.50 | 6.2 | 102% | 100% |
| 1.00 | 5.8 | 101% | 108% |
| 2.00 | 6.1 | 100% | 100% |
| 0 + Tet | 4.7 | 0% | 0% |
| 0.5 + Tet | 5.1 | 81% | 98% |
| 2.0 + Tet | 4.5 | 86% | 117% |

EXAMPLE 6

Analysis of the Integration Site of the Transposon in the L-Rhamnose-Isomerase-Deficient Strain *E. coli* TG10

To characterize the integration site of the transposon Tn10 in greater detail, the rhamnose genes rhaT, rhaB, rhaA and rhaD were studied via PCR (Pfu polymerase) in comparison with TG1 (pDHE681) and TG10 (pDHE681). When rhaA (L-rhamnose isomerase) or the region rhaA-rhaD were amplified with the primers MKe 259/260 and MKe 258/259, respectively, the mutagenized strain TG10 gave no specific amplificate, as opposed to the wild-type strain TG1.

MKe258
(SEQ ID NO: 20)
5'-CCCAAGCTTGGATCATGTTTGCTCCTTACAG
(rhaD 3'End + HindIII)

MKe259
(SEQ ID NO: 21)
5'-GCGAATTCGCATGACCACTCAACTGGAACA
(rhaA 5'End + EcoRI)

MKe260
(SEQ ID NO: 22)
5'-CCCAAGCTTACCCGCGGCGACTCAAAATTT
(rhaA 3'End + HindIII)

EXAMPLE 7

Production of an L-Rhamnose-Isomerase Deficient *E. coli* Strain by Means of Site-Specific Knock-Out To inactivate the L-rhamnose-isomerase (rhaA) the rhaA gene is first amplified with the primers MKe001 and MKe002 and cloned into pBluescriptSK⁺ (XbaI/HindIII digestion and ligation). Thereafter, a frame shift is introduced by restriction digestion with BamHI and filling in with Klenow fragment, followed by ligation, and the corresponding rha* fragment is recloned into the gene replacement vector pKO3 (Link et al. (1997) J Bacteriol 179:6228-6237). The knock-out of the rhaA gene in TG1pDHE1650 by homologous recombination with the rha* construct is carried out as described by Link et al. (Link et al. (1997) J Bacteriol 179:6228-6237) by means of selection on chloramphenicol at 43° C., replica plating on sucrose at 30° C. and subsequent verification on McConkey agar supplemented with 1 g/L rhamnose.

MKe001:
(SEQ ID NO: 23)
5'-ATAAGAATGCGGCCGCATGACCACTCAACTGGAACA-3'

MKe002:
(SEQ ID NO: 24)
5'-CTAGCTCTAGATTACCCGCGGCGACTCAA-3'

EXAMPLE 8

Production of Recombinant Nitrilase with the Rhamnose-Deficient Host Strain TG10

The fed-batch fermentation of TG10 derivatives such as TG10 pDHE1650 pAgro4 pHSG575 is carried out on a modified Riesenberg medium with glycerol as the carbon source and rhamnose as inductor for overexpressing the target protein, in this case nitrilase. Comparably high, and higher, cell densities and enzyme activities were achieved using this strain.
8.1 Fermentation of *E. coli* TG 1
The fermentation of *Escherichia coli* (TG1 pDHE1650 pAgro4 pHSG575) was carried out in a 20 L bioreactor. The reactor, with a working volume of 10 L, was inoculated with 200 ml of preculture from shake flasks. The preculture medium corresponds to the main culture medium.

| Medium: | |
|---|---|
| 40 g | glycerol 99.5% |
| 15 g | tryptone |
| 13.3 g | potassium dihydrogenphosphate |
| 5 g | yeast extract |
| 4 g | diammonium hydrogenphosphate |
| 1.7 g | citric acid |
| 1.1 g | magnesium sulfate heptahydrate |

-continued

| Medium: | | |
|---|---|---|
| 1 mL | trace element solution SL Korz 1000 C | |
| 0.1 mL | Tego KS 911 antifoam | |
| 0.062 g | iron(II) sulfate heptahydrate | |
| 10 mg | thiamine hydrochloride | |
| to 1 L | fully demineralised water | |

The medium is sterilized for 30 min at 121° C. Thereafter, 0.1 g of ampicillin are added under sterile conditions

| Trace element solution | |
|---|---|
| Citric acid * $H_2O$ | 20 g |
| Cobalt(II) chloride hexachloride ($CoCl_2$ * $6H_2O$) | 2.5 g |
| Manganese(II) chloride tetrachloride ($MnCl_2$ * $4H_2O$) | 3.0 g |
| Copper(II) chloride dihydrate ($CuCl_2$ * $2H_2O$) | 0.3 g |
| Boric acid ($H_3BO_3$) | 0.6 g |
| Sodium molybdate dihydrate ($Na_2MoO_4$ * $2H_2O$) | 0.5 g |
| Zinc acetate dihydrate ($Zn(CH_3COO)_2$ * $2H_2O$) | 2.6 g |
| Fully demineralised $H_2O$ to 1 L | |

| Glycerol feed solution | |
|---|---|
| 2 L | fully demineralised water |
| 211 g | sodium sulfate |
| 13.6 g | iron(II) sulfate heptahydrate |
| 8.8 kg | glycerol 99.5% |
| 220 mL | trace element solution |
| Rhamnose feed solution | |
| 703 g | fully demineralised water |
| 297 g | rhamnose monohydrate |

The fermentation is carried at a temperature of 37° C. The aeration is adjusted to between 8-30 L/min and the stirrer speed to 400 to 1500 1/min in order to avoid the $PO_2$ dropping to below 20%. After a fermentation time of 1 hour, the culture is induced with IPTG (0.15 mM). Thereafter, 76 ml of rhamnose feed solution are added. When the rhamnose concentration in the fermenter falls below 1.0 g/L, rhamnose feed solution is metered in. After the amount of glycerol which had been introduced at the beginning has been consumed, glycerol is fed continuously.
Results:

| Time [h] | pO2 [%] | BTM [g/L] | Rhamnose [g/L] | Added rhamnose feed solution [g] | Glycerol [g/L] |
|---|---|---|---|---|---|
| 0 | 0 | 0 | 0 | 0 | 40.0 |
| 2 | 75.8 | 2.3 | 1.70 | 76 | 35.9 |
| 5 | 20.5 | 7.5 | 1.54 | 115 | 33.6 |
| 8 | 33.7 | 17.3 | 1.96 | 244 | 25.4 |
| 11 | 39.3 | 15.7 | 3.11 | 365 | 17.0 |
| 14 | 22.6 | 18.8 | 2.71 | 364 | 8.6 |
| 17 | 30.1 | 21.4 | 1.87 | 404 | 0 |
| 20 | 35.1 | 24.8 | 1.36 | 474 | 0 |
| 23 | 21.5 | 31.8 | 1.18 | 673 | 0 |
| 26 | 23.9 | 28.7 | 1.80 | 970 | 0 |
| 29 | 36.4 | 42.2 | 0.48 | 1234 | 0 |
| 32 | 28.5 | 38.7 | 1.20 | 1639 | 0 |
| 35 | 29.8 | 47.0 | 1.22 | 2033 | 0 |
| 38 | 44.3 | 49.2 | 1.19 | 2474 | 0 |
| 41 | 47.6 | 45.4 | 1.45 | 2879 | 0 |
| 44 | 46.2 | 45.2 | 1.80 | 3237 | 0 |

Activity after 44 h: 57200 U/L 8.2 Fermentation of *E. coli* TG 10

The fermentation of *Escherichia coli* TG10 (pDHE1650 pAgro4 pHSG575) was carried out following the same protocol as in Example 1, except that induction was carried out with 18.5 g of rhamnose feed solution. No rhamnose was subsequently feed in.
Results:

| Time [h] | pO2 [%] | BTM [g/L] | Rhamnose [g/L] | Added rhamnose feed solution [g] | Glycerol [g/L] |
|---|---|---|---|---|---|
| 0 | 0 | 0 | 0.00 | 0 | 40.0 |
| 2 | 71.4 | 2.7 | 0.58 | 18.5 | 38.6 |
| 5 | 20.7 | 7.0 | 0.59 | 18.5 | 36.5 |
| 8 | 21.7 | 13.2 | 0.59 | 18.5 | 26.4 |
| 11 | 31.1 | 16.9 | 0.57 | 18.5 | 13.2 |
| 14 | 44.6 | 19.0 | 0.60 | 18.5 | 0 |
| 17 | 50.5 | 24.0 | 0.58 | 18.5 | 0 |
| 20 | 35.9 | 26.1 | 0.57 | 18.5 | 0 |
| 23 | 33.9 | 33.4 | 0.58 | 18.5 | 0 |
| 26 | 40.4 | 36.0 | 0.57 | 18.5 | 0 |
| 29 | 38.2 | 40.8 | 0.55 | 18.5 | 0 |
| 32 | 34.3 | 45.3 | 0.58 | 18.5 | 0 |
| 35 | 45.7 | 48.7 | 0.50 | 18.5 | 0 |
| 38 | 40.0 | 50.7 | 0.50 | 18.5 | 0 |
| 41 | 31.8 | 52.5 | 0.44 | 18.5 | 0 |
| 44 | 29.5 | 50.0 | 0.44 | 18.5 | 0 |

Activity after 44 h: 59200 U/L 8.3 Activity assay:

50 μl of cell suspension are pipetted to 880 μl of sodium/potassium phosphate buffer (10 mM) and the mixture is heated to 30° C. The reaction is started by addition of 20 μl of methanolic mandelonitrile solution (12%). After 10 minutes, the enzyme reaction is stopped by addition of 50 μl of 1M HCl. The cell biomass is centrifuged off and the mandelic acid concentration in the supernatant is measured by HPLC (ODS Hypersil 100*2.0 mm, mobile phase: 75% $H_3PO_4$ (14.8 mM)/25% methanol; flow rate: 0.5 ml/min; injection volume: 2 μl; column temperature: 40° C.; detection: 210 nm; retention time mandelic acid: 0.9 minutes).

8.4 Determination of the Rhamnose Concentration:

A ceramic filter and a continuously operated roller pump are used for online sampling of the fermenter. The HPLC system is programmed in such a way that a new sample is injected after each analysis has been concluded. In between, the filtrate is pumped from the fermenter into a waste container.

Chromatography Conditions:

| Column: | HPX 87 H, 7.8 × 300 mm |
|---|---|
| Eluent: | 0.005M $H_2SO_4$ |
| Flow rate: | 0.5 mL/min |
| Injection volume: | 1 μL |
| Column temperature: | 55° C. |
| Detection: | RI |

We claim:

1. A method for expressing nucleic acid sequences in prokaryotic host cells by high-density cell fermentation, comprising;
   a) introducing into a prokaryotic host cell at least one DNA construct which is capable of episomal replication in said prokaryotic host cell and comprises a nucleic acid sequence to be expressed under the transcriptional control of an L-rhamnose-inducible promoter, wherein said L-rhamnose-inducible promoter is heterologous with regard to said nucleic acid sequence,
   b) selecting prokaryotic host cells which comprise said DNA construct in episomal form, and
   c) inducing the expression of said nucleic acid sequence by addition of L-rhamnose to a high-density cell culture of said selected prokaryotic host cells, wherein the concentration of L-rhamnose in the medium is from 0.01 g/l to 0.5 g/l,
   wherein the prokaryotic host cell is at least deficient with regard to L-rhamnose isomerase.

2. The method according to claim 1, wherein the prokaryotic host cell is selected from the species of the family Enterobacteriaceae or the order Actinomycetales.

3. The method according to claim 1, wherein the prokaryotic host cell is *Escherichia coli*.

4. The method of claim 1, wherein the L-rhamnose-inducible promoter is the rhaP$_{BAD}$ promoter from *E. coli*.

5. The method of claim 1, wherein the L-rhamnose-inducible promoter comprises at least one RhaS binding element as shown in SEQ ID NO: 5.

6. The method of claim 1, wherein the L-rhamnose-inducible promoter comprises at least one sequence described by SEQ ID NO: 1, 2, 3 or 4.

7. The method according to claim 1, wherein the L-rhamnose isomerase comprises the amino acid sequence of SEQ ID NO: 9.

8. The method according to claim 1, wherein the DNA construct which is capable of episomal replication has a size of not more than 100,000 bases or base pairs.

9. The method according to claim 1, wherein the DNA construct which is capable of episomal replication is selected from the group consisting of circular plasmid vectors, phagemids and cosmids.

10. The method according to claim 1, wherein the prokaryotic host cell has at least one further deficiency with regard to a gene which has a function in the metabolization of rhamnose, where said gene encodes a protein selected from the group consisting of rhamnulose 1-phosphatase (RhaB) and rhamnulose-phosphate aldolase (RhaD).

11. The method according to claim 1, wherein the expression of the nucleic acid sequence to be expressed causes the production of a protein encoded by said nucleic acid sequence.

12. The method according to claim 1, wherein the nucleic acid sequence to be expressed encodes a recombinant protein selected from the group consisting of chymosines, proteases, polymerasen, saccharidases, dehydrogenases, nucleases, glucanases, glucose oxidases, α-amylases, oxidoreductases, peroxidases, laccases, xylanases, phytases, cellulases, collagenases, hemicellulases, lipases, lactases. pectinases, amyloglucosidases, glucoamylases, pullulanases, glucose isomerases, nitrilases, esterases, nitrile hydratases, amidases, oxygenases, oxynitrilases, lyases, lactonases, carboxylases, collagenases, cellulases, serum albumins, factor VII, factor VIII, factor IX, factor X, tissue plasminogen factors, protein C, von Willebrand factors, antithrombins. erythropoietins, colony-stimulating factors. cytokins, interleukins, insulins, integrins, addressins, selectins, antibodies, antibody fragments, structural proteins, collagen, fibroins, elastins, tubulins, actins, myosins, growth factors, cell-cycle proteins, vaccines, fibrinogens and thrombins.

13. An isolated prokaryotic host cell capable of producing recombinant proteins by high-density cell fermentation, wherein said host cell is at least deficient with regard to L-rhamnose isomerase and comprises at least one DNA construct, wherein the at least one DNA construct is capable of replication in said host cell and comprises a nucleic acid sequence to be expressed under the transcriptional control of an L-rhamnose-inducible promoter in the presence of L-rhamnose at a concentration from 0.01 g/l to 0.5 g/l in high-density cell fermentation, wherein said L-rhamnose-inducible promoter is heterologous with regard to said nucleic acid sequence.

14. A process for the production of foodstuffs, feedstuffs, enzymes, chemicals, pharmaceuticals or fine chemicals, which comprises culturing the isolated prokaryotic host cell of claim 13 under high-density cell culture conditions allowing expression of said nucleic acid sequence for preparing foodstuffs, feedstuffs, enzymes, chemicals, pharmaceuticals or fine chemicals, and isolating the foodstuffs, feedstuffs, enzymes, chemicals, pharmaceuticals or fine chemicals produced.

15. A method for the production of recombinant proteins, enzymes or fine chemicals, comprising culturing the isolated prokaryotic host cell of claim 13 under high-density cell culture conditions allowing expression of said nucleic acid sequence for producing recombinant proteins, enzymes and fine chemicals, and isolating the recombinant proteins, enzymes and fine chemicals produced.

* * * * *

SEQUENCE LISTING

<160> NUMBER OF SEQ ID NOS: 24

<210> SEQ ID NO 1
<211> LENGTH: 2046
<212> TYPE: DNA
<213> ORGANISM: Escherichia coli
<220> FEATURE:
<221> NAME/KEY: misc_feature
<222> LOCATION: (288)..(1121)
<223> OTHER INFORMATION: coding for rhaS (positive regulator of rhaBAD operon)
<220> FEATURE:
<221> NAME/KEY: misc_feature
<222> LOCATION: (1108)..(2043)
<223> OTHER INFORMATION: coding for rhaR (positive regulator of rhaRS operon)
<220> FEATURE:
<221> NAME/KEY: protein_bind
<222> LOCATION: (56)..(72)
<223> OTHER INFORMATION: potential RhaS binding site
<220> FEATURE:
<221> NAME/KEY: protein_bind
<222> LOCATION: (89)..(105)
<223> OTHER INFORMATION: potential RhaS binding site
<220> FEATURE:
<221> NAME/KEY: protein_bind
<222> LOCATION: (172)..(203)
<223> OTHER INFORMATION: potential RhaR binding site
<220> FEATURE:
<221> NAME/KEY: protein_bind
<222> LOCATION: (210)..(241)
<223> OTHER INFORMATION: potential RhaR binding site
<220> FEATURE:
<221> NAME/KEY: misc_feature
<222> LOCATION: (24)
<223> OTHER INFORMATION: potential start of transcription (complement)

<400> SEQUENCE: 1

```
aatgtgatcc tgctgaattt cattacgacc agtctaaaaa gcgcctgaat tcgcgacctt      60
ctcgttactg acaggaaaat gggccattgg caaccaggga agatgaacg tgatgatgtt     120 cacaatttgc tgaattgtgg tgatgtgatg ctcaccgcat ttcctgaaaa ttcacgctgt    180
atcttgaaaa atcgacgttt tttacgtggt tttccgtcga aaatttaagg taagaacctg    240
acctcgtgat tactatttcg ccgtgttgac gacatcagga ggccagtatg accgtattac    300
atagtgtgga ttttttttccg tctggtaacg cgtccgtggc gatagaaccc cggctcccgc   360
aggcggattt tcctgaacat catcatgatt ttcatgaaat tgtgattgtc gaacatggca    420
cgggtattca tgtgtttaat gggcagcccct ataccatcac cggtggcacg gtctgtttcg   480
tacgcgatca tgatcggcat ctgtatgaac ataccgataa tctgtgtctg accaatgtgc    540
tgtatcgctc gccggatcga tttcagtttc tcgccgggct gaatcagttg ctgccacaag    600
agctggatgg gcagtatccg tctcactggc gcgttaacca cagcgtattg cagcaggtgc    660
gacagctggt tgcacagatg gaacagcagg aagggggaaaa tgatttaccc tcgaccgcca    720
gtcgcgagat cttgtttatg caattactgc tcttgctgcg taaaagcagt ttgcaggaga    780
acctggaaaa cagcgcatca cgtctcaact tgcttctggc ctggctggag gaccattttg    840
ccgatgaggt gaattgggat gccgtggcgg atcaattttc tctttcactg cgtacgctac    900
atcggcagct taagcagcaa acgggactga cgcctcagcg atacctgaac cgcctgcgac    960
tgatgaaagc ccgacatctg ctacgccaca gcgaggccag cgttactgac atcgcctatc   1020
gctgtggatt cagcgacagt aaccactttt cgacgctttt tcgccgagag tttaactggt   1080
caccgcgtga tattgccag ggacgggatg gcttctgca ataacgcgaa tcttctcaac     1140
gtatttgtac gccatattgc gaataatcaa cttcgttctc tggccgaggt agccacggtg   1200
```

-continued

```
gcgcatcagt taaaacttct caaagatgat ttttttgcca gcgaccagca ggcagtcgct    1260
gtggctgacc gttatccgca agatgtcttt gctgaacata cacatgattt ttgtgagctg    1320
gtgattgtct ggcgcggtaa tggcctgcat gtactcaacg atcgcccttta tcgcattacc    1380 cgtggcgatc tcttttacat tcatgctgac gataaacact cctacgcttc cgttaacgat    1440
ctggttttgc agaatattat ttattgcccg gagcgtctga agctgaatct tgactggcag    1500
ggggcgattc cgggatttaa cgccagcgca gggcaaccac actggcgctt aggtagcatg    1560
gggatggcgc aggcgcggca ggttatcggt cagcttgagc atgaaagtag tcagcatgtg    1620
ccgtttgcta cgaaatggc tgagttgctg ttcgggcagt tggtgatgtt gctgaatcgc    1680
catcgttaca ccagtgattc gttgccgcca acatccagcg aaacgttgct ggataagctg    1740 attcccggc tggcggctag cctgaaaagt ccctttgcgc tggataaatt ttgtgatgag    1800
gcatcgtgca gtgagcgcgt tttgcgtcag caatttcgcc agcagactgg aatgaccatc    1860
aatcaatatc tgcgacaggt cagagtgtgt catgcgcaat atcttctcca gcatagccgc    1920
ctgttaatca gtgatatttc gaccgaatgt ggctttgaag atagtaacta ttttttcggtg    1980 gtgtttaccc gggaaaccgg gatgacgccc agccagtggc gtcatctcaa ttcgcagaaa    2040
gattaa                                                                2046
```

<210> SEQ ID NO 2
<211> LENGTH: 287
<212> TYPE: DNA
<213> ORGANISM: Escherichia coli
<220> FEATURE:
<221> NAME/KEY: promoter
<222> LOCATION: (1)..(287)
<223> OTHER INFORMATION: rhaBAD promoter fragment containing rhaS and
      rhaR binding sites

<400> SEQUENCE: 2

```
actggcctcc tgatgtcgtc aacacggcga aatagtaatc acgaggtcag gttcttacct     60
taaattttcg acggaaaacc acgtaaaaaa cgtcgatttt tcaagataca gcgtgaattt    120
tcaggaaatg cggtgagcat cacatcacca caattcagca aattgtgaac atcatcacgt    180
tcatctttcc ctggttgcca atggcccatt ttcctgtcag taacgagaag gtcgcgaatt    240
caggcgcttt ttagactggt cgtaatgaaa ttcagcagga tcacatt                  287
```

<210> SEQ ID NO 3
<211> LENGTH: 125
<212> TYPE: DNA
<213> ORGANISM: Escherichia coli
<220> FEATURE:
<221> NAME/KEY: promoter
<222> LOCATION: (1)..(125)
<223> OTHER INFORMATION: rhaBAD promoter fragment containing RhaS
      binding site

<400> SEQUENCE: 3

```
ttgtgaacat catcacgttc atctttccct ggttgccaat ggcccatttt cctgtcagta     60
acgagaaggt cgcgaattca ggcgcttttt agactggtcg taatgaaatt cagcaggatc    120
acatt                                                                125
```

<210> SEQ ID NO 4
<211> LENGTH: 123
<212> TYPE: DNA
<213> ORGANISM: Escherichia coli
<220> FEATURE:

```
<221> NAME/KEY: promoter
<222> LOCATION: (1)..(123)
<223> OTHER INFORMATION: rhaBAD promoter fragment containing RhaS
      binding site

<400> SEQUENCE: 4
atcaccacaa ttcagcaaat tgtgaacatc atcacgttca tctttccctg gttgccaatg      60
gcccattttc ctgtcagtaa cgagaaggtc gcgaattcag gcgcttttta gactggtcgt     120
aat                                                                   123

<210> SEQ ID NO 5
<211> LENGTH: 51
<212> TYPE: DNA
<213> ORGANISM: Escherichia coli
<220> FEATURE:
<221> NAME/KEY: misc_feature
<222> LOCATION: (1)..(51)
<223> OTHER INFORMATION: palindromic RhaS binding site of rhaBAD
      promoter

<400> SEQUENCE: 5
atctttccct ggttgccaat ggcccatttt cctgtcagta acgagaaggt c               51

<210> SEQ ID NO 6
<211> LENGTH: 1071
<212> TYPE: DNA
<213> ORGANISM: Alcaligenes faecalis
<220> FEATURE:
<221> NAME/KEY: CDS
<222> LOCATION: (1)..(1068)
<223> OTHER INFORMATION: coding for nitrilase

<400> SEQUENCE: 6
```

| | | | | | | | | | | | | | | | | |
|---|---|---|---|---|---|---|---|---|---|---|---|---|---|---|---|---|
| atg | cag | aca | aga | aaa | atc | gtc | cgg | gca | gcc | gcc | gta | cag | gcc | gcc | tct | 48 |
| Met | Gln | Thr | Arg | Lys | Ile | Val | Arg | Ala | Ala | Ala | Val | Gln | Ala | Ala | Ser | |
| 1 | | | | 5 | | | | | 10 | | | | | 15 | | |
| ccc | aac | tac | gat | ctg | gca | acg | ggt | gtt | gat | aaa | acc | att | gag | ctg | gct | 96 |
| Pro | Asn | Tyr | Asp | Leu | Ala | Thr | Gly | Val | Asp | Lys | Thr | Ile | Glu | Leu | Ala | |
| | | | 20 | | | | | 25 | | | | | 30 | | | |
| cgt | cag | gcc | cgc | gat | gag | ggc | tgt | gac | ctg | atc | gtg | ttt | ggt | gaa | acc | 144 |
| Arg | Gln | Ala | Arg | Asp | Glu | Gly | Cys | Asp | Leu | Ile | Val | Phe | Gly | Glu | Thr | |
| | 35 | | | | | 40 | | | | | 45 | | | | | |
| tgg | ctg | ccc | gga | tat | ccc | ttc | cac | gtc | tgg | ctg | ggc | gca | ccg | gcc | tgg | 192 |
| Trp | Leu | Pro | Gly | Tyr | Pro | Phe | His | Val | Trp | Leu | Gly | Ala | Pro | Ala | Trp | |
| 50 | | | | | 55 | | | | | 60 | | | | | | |
| tcg | ctg | aaa | tac | agt | gcc | cgc | tac | tat | gcc | aac | tcg | ctc | tcg | ctg | gac | 240 |
| Ser | Leu | Lys | Tyr | Ser | Ala | Arg | Tyr | Tyr | Ala | Asn | Ser | Leu | Ser | Leu | Asp | |
| 65 | | | | | 70 | | | | | 75 | | | | | 80 | |
| agt | gca | gag | ttt | caa | cgc | att | gcc | cag | gcc | gca | cgg | acc | ttg | ggt | att | 288 |
| Ser | Ala | Glu | Phe | Gln | Arg | Ile | Ala | Gln | Ala | Ala | Arg | Thr | Leu | Gly | Ile | |
| | | | | 85 | | | | | 90 | | | | | 95 | | |
| ttc | atc | gca | ctg | ggt | tat | agc | gag | cgc | agc | ggc | ggc | agc | ctt | tac | ctg | 336 |
| Phe | Ile | Ala | Leu | Gly | Tyr | Ser | Glu | Arg | Ser | Gly | Gly | Ser | Leu | Tyr | Leu | |
| | | | 100 | | | | | 105 | | | | | 110 | | | |
| ggc | caa | tgc | ctg | atc | gac | gac | aag | ggc | gag | atg | ctg | tgg | tcg | cgt | cgc | 384 |
| Gly | Gln | Cys | Leu | Ile | Asp | Asp | Lys | Gly | Glu | Met | Leu | Trp | Ser | Arg | Arg | |
| | 115 | | | | | 120 | | | | | 125 | | | | | |
| aaa | ctc | aaa | ccc | acg | cat | gta | gag | cgc | acc | gta | ttt | ggt | gaa | ggt | tat | 432 |
| Lys | Leu | Lys | Pro | Thr | His | Val | Glu | Arg | Thr | Val | Phe | Gly | Glu | Gly | Tyr | |
| 130 | | | | | 135 | | | | | 140 | | | | | | |
| gcc | cgt | gat | ctg | att | gtg | tcc | gac | aca | gaa | ctg | gga | cgc | gtc | ggt | gct | 480 |
| Ala | Arg | Asp | Leu | Ile | Val | Ser | Asp | Thr | Glu | Leu | Gly | Arg | Val | Gly | Ala | |
| 145 | | | | | 150 | | | | | 155 | | | | | 160 | |

```
cta tgc tgc tgg gag cat ttg tcg ccc ttg agc aag tac gcg ctg tac        528
Leu Cys Cys Trp Glu His Leu Ser Pro Leu Ser Lys Tyr Ala Leu Tyr
                165                 170                 175 tcc cag cat gaa gcc att cac att gct gcc tgg ccg tcg ttt tcg cta        576
Ser Gln His Glu Ala Ile His Ile Ala Ala Trp Pro Ser Phe Ser Leu
        180                 185                 190 tac agc gaa cag gcc cac gcc ctc agt gcc aag gtg aac atg gct gcc        624
Tyr Ser Glu Gln Ala His Ala Leu Ser Ala Lys Val Asn Met Ala Ala
    195                 200                 205 tcg caa atc tat tcg gtt gaa ggc cag tgc ttt acc atc gcc gcc agc        672
Ser Gln Ile Tyr Ser Val Glu Gly Gln Cys Phe Thr Ile Ala Ala Ser
210                 215                 220 agt gtg gtc acc caa gag acg cta gac atg ctg gaa gtg ggt gaa cac        720
Ser Val Val Thr Gln Glu Thr Leu Asp Met Leu Glu Val Gly Glu His
225                 230                 235                 240 aac gcc ccc ttg ctg aaa gtg ggc ggc ggc agt tcc atg att ttt gcg        768
Asn Ala Pro Leu Leu Lys Val Gly Gly Gly Ser Ser Met Ile Phe Ala
                245                 250                 255 ccg gac gga cgc aca ctg gct ccc tac ctg cct cac gat gcc gag ggc        816
Pro Asp Gly Arg Thr Leu Ala Pro Tyr Leu Pro His Asp Ala Glu Gly
            260                 265                 270 ttg atc att gcc gat ctg aat atg gag gag att gcc ttc gcc aaa gcg        864
Leu Ile Ile Ala Asp Leu Asn Met Glu Glu Ile Ala Phe Ala Lys Ala
        275                 280                 285 atc aat gac ccc gta ggc cac tat tcc aaa ccc gag gcc acc cgt ctg        912
Ile Asn Asp Pro Val Gly His Tyr Ser Lys Pro Glu Ala Thr Arg Leu
    290                 295                 300 gtg ctg gac ttg ggg cac cga gac ccc atg act cgg gtg cac tcc aaa        960
Val Leu Asp Leu Gly His Arg Asp Pro Met Thr Arg Val His Ser Lys
305                 310                 315                 320 agc gtg acc agg gaa gag gct ccc gag caa ggt gtg caa agc aag att       1008
Ser Val Thr Arg Glu Glu Ala Pro Glu Gln Gly Val Gln Ser Lys Ile
                325                 330                 335 gcc tca gtc gct atc agc cat cca cag gac tcg gac aca ctg cta gtg       1056
Ala Ser Val Ala Ile Ser His Pro Gln Asp Ser Asp Thr Leu Leu Val
            340                 345                 350 caa gag ccg tct tga                                                    1071
Gln Glu Pro Ser
        355
```

<210> SEQ ID NO 7
<211> LENGTH: 356
<212> TYPE: PRT
<213> ORGANISM: Alcaligenes faecalis

<400> SEQUENCE: 7

```
Met Gln Thr Arg Lys Ile Val Arg Ala Ala Val Gln Ala Ala Ser
 1               5                  10                  15

Pro Asn Tyr Asp Leu Ala Thr Gly Val Asp Lys Thr Ile Glu Leu Ala
                20                  25                  30

Arg Gln Ala Arg Asp Glu Gly Cys Asp Leu Ile Val Phe Gly Glu Thr
            35                  40                  45

Trp Leu Pro Gly Tyr Pro Phe His Val Trp Leu Gly Ala Pro Ala Trp
        50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95
```

```
Phe Ile Ala Leu Gly Tyr Ser Glu Arg Ser Gly Gly Ser Leu Tyr Leu
                100                 105                 110

Gly Gln Cys Leu Ile Asp Asp Lys Gly Glu Met Leu Trp Ser Arg Arg
            115                 120                 125

Lys Leu Lys Pro Thr His Val Glu Arg Thr Val Phe Gly Glu Gly Tyr
        130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
    210                 215                 220

Ser Val Val Thr Gln Glu Thr Leu Asp Met Leu Glu Val Gly Glu His
225                 230                 235                 240

Asn Ala Pro Leu Leu Lys Val Gly Gly Ser Ser Met Ile Phe Ala
                245                 250                 255

Pro Asp Gly Arg Thr Leu Ala Pro Tyr Leu Pro His Asp Ala Glu Gly
            260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
    290                 295                 300

Val Leu Asp Leu Gly His Arg Asp Pro Met Thr Arg Val His Ser Lys
305                 310                 315                 320

Ser Val Thr Arg Glu Glu Ala Pro Glu Gln Gly Val Gln Ser Lys Ile
                325                 330                 335

Ala Ser Val Ala Ile Ser His Pro Gln Asp Ser Asp Thr Leu Leu Val
            340                 345                 350

Gln Glu Pro Ser
        355

<210> SEQ ID NO 8
<211> LENGTH: 1260
<212> TYPE: DNA
<213> ORGANISM: Escherichia coli
<220> FEATURE:
<221> NAME/KEY: CDS
<222> LOCATION: (1)..(1257)
<223> OTHER INFORMATION: coding for rhaA (L-rhamnose isomerase)

<400> SEQUENCE: 8 atg acc act caa ctg gaa cag gcc tgg gag cta gcg aaa cag cgt ttc      48
Met Thr Thr Gln Leu Glu Gln Ala Trp Glu Leu Ala Lys Gln Arg Phe
1               5                   10                  15 gcg gcg gtg ggg att gat gtc gag gag gcg ctg cgc caa ctt gat cgt      96
Ala Ala Val Gly Ile Asp Val Glu Glu Ala Leu Arg Gln Leu Asp Arg
                20                  25                  30 tta ccc gtt tca atg cac tgc tgg cag ggc gat gat gtt tcc ggt ttt     144
Leu Pro Val Ser Met His Cys Trp Gln Gly Asp Asp Val Ser Gly Phe
            35                  40                  45 gaa aac ccg gaa ggt tcg ctg acc ggg ggg att cag gcc aca ggc aat     192
Glu Asn Pro Glu Gly Ser Leu Thr Gly Gly Ile Gln Ala Thr Gly Asn
    50                  55                  60
```

-continued

| | | |
|---|---|---|
| tat ccg ggc aaa gcg cgt aat gcc agt gag cta cgt gcc gat ctg gaa<br>Tyr Pro Gly Lys Ala Arg Asn Ala Ser Glu Leu Arg Ala Asp Leu Glu<br>65                   70                   75                 80 | 240 |
| cag gct atg cgg ctg att ccg ggg ccg aaa cgg ctt aat tta cat gcc<br>Gln Ala Met Arg Leu Ile Pro Gly Pro Lys Arg Leu Asn Leu His Ala<br>85                   90                   95 | 288 |
| atc tat ctg gaa tca gat acg cca gtc tcg cgc gac cag atc aaa cca<br>Ile Tyr Leu Glu Ser Asp Thr Pro Val Ser Arg Asp Gln Ile Lys Pro<br>100                 105                 110 | 336 |
| gag cac ttc aaa aac tgg gtt gaa tgg gcg aaa gcc aat cag ctc ggt<br>Glu His Phe Lys Asn Trp Val Glu Trp Ala Lys Ala Asn Gln Leu Gly<br>115                 120                 125 | 384 |
| ctg gat ttt aac ccc tcc tgc ttt tcg cat ccg cta agc gcc gat ggc<br>Leu Asp Phe Asn Pro Ser Cys Phe Ser His Pro Leu Ser Ala Asp Gly<br>130                 135                 140 | 432 |
| ttt acg ctt tcc cat gcc gac gac agc att cgc cag ttc tgg att gat<br>Phe Thr Leu Ser His Ala Asp Asp Ser Ile Arg Gln Phe Trp Ile Asp<br>145                 150                 155                 160 | 480 |
| cac tgc aaa gcc agc cgt cgc gtt tcg gcc tat ttt ggc gag caa ctc<br>His Cys Lys Ala Ser Arg Arg Val Ser Ala Tyr Phe Gly Glu Gln Leu<br>165                 170                 175 | 528 |
| ggc aca cca tcg gtg atg aac atc tgg atc ccg gat ggt atg aaa gat<br>Gly Thr Pro Ser Val Met Asn Ile Trp Ile Pro Asp Gly Met Lys Asp<br>180                 185                 190 | 576 |
| atc acc gtt gac cgt ctc gcc ccg cgt cag cgt ctg ctg gca gca ctg<br>Ile Thr Val Asp Arg Leu Ala Pro Arg Gln Arg Leu Leu Ala Ala Leu<br>195                 200                 205 | 624 |
| gat gag gtg atc agc gag aag cta aac cct gcg cac cat atc gac gcc<br>Asp Glu Val Ile Ser Glu Lys Leu Asn Pro Ala His His Ile Asp Ala<br>210                 215                 220 | 672 |
| gtt gag agc aaa ttg ttt ggc att ggc gca gag agc tac acg gtt ggc<br>Val Glu Ser Lys Leu Phe Gly Ile Gly Ala Glu Ser Tyr Thr Val Gly<br>225                 230                 235                 240 | 720 |
| tcc aat gag ttt tac atg ggg tat gcc acc agc cgc cag act gcg ctg<br>Ser Asn Glu Phe Tyr Met Gly Tyr Ala Thr Ser Arg Gln Thr Ala Leu<br>245                 250                 255 | 768 |
| tgc ctg gac gcc ggg cac ttc cac ccg act gaa gtg att tcc gac aag<br>Cys Leu Asp Ala Gly His Phe His Pro Thr Glu Val Ile Ser Asp Lys<br>260                 265                 270 | 816 |
| att tcc gcc gcc atg ctg tat gtg ccg cag ttg ctg ctg cac gtc agc<br>Ile Ser Ala Ala Met Leu Tyr Val Pro Gln Leu Leu Leu His Val Ser<br>275                 280                 285 | 864 |
| cgt ccg gtt cgc tgg gac agc gat cac gta gtg ctg ctg gat gat gaa<br>Arg Pro Val Arg Trp Asp Ser Asp His Val Val Leu Leu Asp Asp Glu<br>290                 295                 300 | 912 |
| acc cag gca att gcc agt gag att gtg cgt cac gat ctg ttt gac cgg<br>Thr Gln Ala Ile Ala Ser Glu Ile Val Arg His Asp Leu Phe Asp Arg<br>305                 310                 315                 320 | 960 |
| gtg cat atc ggc ctt gac ttc ttc gat gcc tct atc aac cgc att gcc<br>Val His Ile Gly Leu Asp Phe Phe Asp Ala Ser Ile Asn Arg Ile Ala<br>325                 330                 335 | 1008 |
| gcg tgg gtc att ggt aca cgc aat atg aaa aaa gcc ctg ctg cgt gcg<br>Ala Trp Val Ile Gly Thr Arg Asn Met Lys Lys Ala Leu Leu Arg Ala<br>340                 345                 350 | 1056 |
| ttg ctg gaa cct acc gct gac gtg cgc aag ctg gaa gcg gcg ggc gat<br>Leu Leu Glu Pro Thr Ala Asp Val Arg Lys Leu Glu Ala Ala Gly Asp<br>355                 360                 365 | 1104 |
| tac act gcg cgt ctg gca ctg ctg gaa gag cag aaa tcg ttg ccg tgg<br>Tyr Thr Ala Arg Leu Ala Leu Leu Glu Glu Gln Lys Ser Leu Pro Trp<br>370                 375                 380 | 1152 |

```
cag gcg gtc tgg gaa atg tat tgc caa cgt cac gat acg cca gca ggt    1200
Gln Ala Val Trp Glu Met Tyr Cys Gln Arg His Asp Thr Pro Ala Gly
385                 390                 395                 400 agc gaa tgg ctg gag agc gtg cgg gct tat gag aaa gaa att ttg agt    1248
Ser Glu Trp Leu Glu Ser Val Arg Ala Tyr Glu Lys Glu Ile Leu Ser
                405                 410                 415 cgc cgc ggg taa                                                    1260
Arg Arg Gly <210> SEQ ID NO 9
<211> LENGTH: 419
<212> TYPE: PRT
<213> ORGANISM: Escherichia coli

<400> SEQUENCE: 9

Met Thr Thr Gln Leu Glu Gln Ala Trp Glu Leu Ala Lys Gln Arg Phe
 1               5                  10                  15

Ala Ala Val Gly Ile Asp Val Glu Glu Ala Leu Arg Gln Leu Asp Arg
                20                  25                  30

Leu Pro Val Ser Met His Cys Trp Gln Gly Asp Asp Val Ser Gly Phe
            35                  40                  45

Glu Asn Pro Glu Gly Ser Leu Thr Gly Gly Ile Gln Ala Thr Gly Asn
        50                  55                  60

Tyr Pro Gly Lys Ala Arg Asn Ala Ser Glu Leu Arg Ala Asp Leu Glu
 65                 70                  75                  80

Gln Ala Met Arg Leu Ile Pro Gly Pro Lys Arg Leu Asn Leu His Ala
                85                  90                  95

Ile Tyr Leu Glu Ser Asp Thr Pro Val Ser Arg Asp Gln Ile Lys Pro
           100                 105                 110

Glu His Phe Lys Asn Trp Val Glu Trp Ala Lys Ala Asn Gln Leu Gly
       115                 120                 125

Leu Asp Phe Asn Pro Ser Cys Phe Ser His Pro Leu Ser Ala Asp Gly
   130                 135                 140

Phe Thr Leu Ser His Ala Asp Asp Ser Ile Arg Gln Phe Trp Ile Asp
145                 150                 155                 160

His Cys Lys Ala Ser Arg Arg Val Ser Ala Tyr Phe Gly Glu Gln Leu
                165                 170                 175

Gly Thr Pro Ser Val Met Asn Ile Trp Ile Pro Asp Gly Met Lys Asp
            180                 185                 190

Ile Thr Val Asp Arg Leu Ala Pro Arg Gln Arg Leu Leu Ala Ala Leu
        195                 200                 205

Asp Glu Val Ile Ser Glu Lys Leu Asn Pro Ala His His Ile Asp Ala
    210                 215                 220

Val Glu Ser Lys Leu Phe Gly Ile Gly Ala Glu Ser Tyr Thr Val Gly
225                 230                 235                 240

Ser Asn Glu Phe Tyr Met Gly Tyr Ala Thr Ser Arg Gln Thr Ala Leu
                245                 250                 255

Cys Leu Asp Ala Gly His Phe His Pro Thr Glu Val Ile Ser Asp Lys
            260                 265                 270

Ile Ser Ala Ala Met Leu Tyr Val Pro Gln Leu Leu Leu His Val Ser
        275                 280                 285

Arg Pro Val Arg Trp Asp Ser Asp His Val Val Leu Leu Asp Asp Glu
    290                 295                 300

Thr Gln Ala Ile Ala Ser Glu Ile Val Arg His Asp Leu Phe Asp Arg
305                 310                 315                 320
```

```
Val His Ile Gly Leu Asp Phe Phe Asp Ala Ser Ile Asn Arg Ile Ala
            325                 330                 335

Ala Trp Val Ile Gly Thr Arg Asn Met Lys Lys Ala Leu Leu Arg Ala
            340                 345                 350

Leu Leu Glu Pro Thr Ala Asp Val Arg Lys Leu Glu Ala Ala Gly Asp
            355                 360                 365

Tyr Thr Ala Arg Leu Ala Leu Leu Glu Glu Gln Lys Ser Leu Pro Trp
    370                 375                 380

Gln Ala Val Trp Glu Met Tyr Cys Gln Arg His Asp Thr Pro Ala Gly
385                 390                 395                 400

Ser Glu Trp Leu Glu Ser Val Arg Ala Tyr Lys Glu Ile Leu Ser
            405                 410                 415

Arg Arg Gly

<210> SEQ ID NO 10
<211> LENGTH: 1470
<212> TYPE: DNA
<213> ORGANISM: Escherichia coli
<220> FEATURE:
<221> NAME/KEY: CDS
<222> LOCATION: (1)..(1467)
<223> OTHER INFORMATION: coding for rhaB (rhamnolukinase)

<400> SEQUENCE: 10 atg acc ttt cgc aat tgt gtc gcc gtc gat ctc ggc gca tcc agt ggg      48
Met Thr Phe Arg Asn Cys Val Ala Val Asp Leu Gly Ala Ser Ser Gly
1                5                  10                  15 cgc gtg atg ctg gcg cgt tac gag cgt gaa tgc cgc agc ctg acg ctg      96
Arg Val Met Leu Ala Arg Tyr Glu Arg Glu Cys Arg Ser Leu Thr Leu
                20                  25                  30 cgc gaa atc cat cgt ttt aac aat ggg ctg cat agt cag aac ggc tat     144
Arg Glu Ile His Arg Phe Asn Asn Gly Leu His Ser Gln Asn Gly Tyr
            35                  40                  45 gtc acc tgg gat gtg gat agc ctt gaa agt gcc att cgc ctt gga tta     192
Val Thr Trp Asp Val Asp Ser Leu Glu Ser Ala Ile Arg Leu Gly Leu
        50                  55                  60 aac aag gtg tgc gag gaa ggg att cgt atc gat agc att ggg att gat     240
Asn Lys Val Cys Glu Glu Gly Ile Arg Ile Asp Ser Ile Gly Ile Asp
65                  70                  75                  80 acc tgg ggc gtg gac ttt gtg ctg ctc gac caa cag ggt cag cgt gtg     288
Thr Trp Gly Val Asp Phe Val Leu Leu Asp Gln Gln Gly Gln Arg Val
                85                  90                  95 ggc ctg ccc gtt gct tat cgc gat agc cgc acc aat ggc cta atg gcg     336
Gly Leu Pro Val Ala Tyr Arg Asp Ser Arg Thr Asn Gly Leu Met Ala
                100                 105                 110 cag gca caa caa caa ctc ggc aaa cgc gat att tat caa cgt agc ggc     384
Gln Ala Gln Gln Gln Leu Gly Lys Arg Asp Ile Tyr Gln Arg Ser Gly
            115                 120                 125 atc cag ttt ctg ccc ttc aat acg ctt tat cag ttg cgt gcg ctg acg     432
Ile Gln Phe Leu Pro Phe Asn Thr Leu Tyr Gln Leu Arg Ala Leu Thr
        130                 135                 140 gag caa caa cct gaa ctt att cca cac att gct cac gct ctg ctg atg     480
Glu Gln Gln Pro Glu Leu Ile Pro His Ile Ala His Ala Leu Leu Met
145                 150                 155                 160 ccg gat tac ttc agt tat cgc ctg acc ggc aag atg aac tgg gaa tat     528
Pro Asp Tyr Phe Ser Tyr Arg Leu Thr Gly Lys Met Asn Trp Glu Tyr
                165                 170                 175 acc aac gcc acg acc acg caa ctg gtc aat atc aat agc gac gac tgg     576
Thr Asn Ala Thr Thr Thr Gln Leu Val Asn Ile Asn Ser Asp Asp Trp
```

```
                     180                 185                 190
gac gag tcg cta ctg gcg tgg agc ggg gcc aac aaa gcc tgg ttt ggt      624
Asp Glu Ser Leu Leu Ala Trp Ser Gly Ala Asn Lys Ala Trp Phe Gly
        195                 200                 205 cgc ccg acg cat ccg ggt aat gtc ata ggt cac tgg att tgc ccg cag      672
Arg Pro Thr His Pro Gly Asn Val Ile Gly His Trp Ile Cys Pro Gln
    210                 215                 220 ggt aat gag att cca gtg gtc gcc gtt gcc agc cat gat acc gcc agc      720
Gly Asn Glu Ile Pro Val Val Ala Val Ala Ser His Asp Thr Ala Ser
225                 230                 235                 240 gcg gtt atc gcc tcg ccg tta aac ggc tca cgt gct gct tat ctc tct      768
Ala Val Ile Ala Ser Pro Leu Asn Gly Ser Arg Ala Ala Tyr Leu Ser
                245                 250                 255 tct ggc acc tgg tca ttg atg ggc ttc gaa agc cag acg cca ttt acc      816
Ser Gly Thr Trp Ser Leu Met Gly Phe Glu Ser Gln Thr Pro Phe Thr
            260                 265                 270 aat gac acg gca ctg gca gcc aac atc acc aat gaa ggc ggg gcg gaa      864
Asn Asp Thr Ala Leu Ala Ala Asn Ile Thr Asn Glu Gly Gly Ala Glu
        275                 280                 285 ggt cgc tat cgg gtg ctg aaa aat att atg ggc tta tgg ctg ctt cag      912
Gly Arg Tyr Arg Val Leu Lys Asn Ile Met Gly Leu Trp Leu Leu Gln
    290                 295                 300 cga gtg ctt cag gag cag caa atc aac gat ctt ccg gcg ctt atc tcc      960
Arg Val Leu Gln Glu Gln Gln Ile Asn Asp Leu Pro Ala Leu Ile Ser
305                 310                 315                 320 gcg aca cag gca ctt ccg gct tgc cgc ttc att atc aat ccc aat gac     1008
Ala Thr Gln Ala Leu Pro Ala Cys Arg Phe Ile Ile Asn Pro Asn Asp
                325                 330                 335 gat cgc ttt att aat cct gag acg atg tgc agc gaa att cag gct gcg     1056
Asp Arg Phe Ile Asn Pro Glu Thr Met Cys Ser Glu Ile Gln Ala Ala
            340                 345                 350 tgt cgg gaa acg gcg caa ccg atc ccg gaa agt gat gct gaa ctg gcg     1104
Cys Arg Glu Thr Ala Gln Pro Ile Pro Glu Ser Asp Ala Glu Leu Ala
        355                 360                 365 cgc tgc att ttc gac agt ctg gcg ctg ctg tat gcc gat gtg ttg cat     1152
Arg Cys Ile Phe Asp Ser Leu Ala Leu Leu Tyr Ala Asp Val Leu His
    370                 375                 380 gag ctg gcg cag ctg cgc ggt gaa gat ttc tcg caa ctg cat att gtc     1200
Glu Leu Ala Gln Leu Arg Gly Glu Asp Phe Ser Gln Leu His Ile Val
385                 390                 395                 400 ggc gga ggc tgc cag aac acg ctg ctc aac cag cta tgc gcc gat gcc     1248
Gly Gly Gly Cys Gln Asn Thr Leu Leu Asn Gln Leu Cys Ala Asp Ala
                405                 410                 415 tgc ggt att cgg gtg atc gcc ggg cct gtt gaa gcc tcg acg ctc ggc     1296
Cys Gly Ile Arg Val Ile Ala Gly Pro Val Glu Ala Ser Thr Leu Gly
            420                 425                 430 aat atc ggc atc cag tta atg acg ctg gat gaa ctc aac aat gtg gat     1344
Asn Ile Gly Ile Gln Leu Met Thr Leu Asp Glu Leu Asn Asn Val Asp
        435                 440                 445 gat ttc cgt cag gtc gtc agc acc acc gcg aat ctg acc acc ttt acc     1392
Asp Phe Arg Gln Val Val Ser Thr Thr Ala Asn Leu Thr Thr Phe Thr
    450                 455                 460 cct aat cct gac agt gaa att gcc cac tat gtg gcg cag att cac tct     1440
Pro Asn Pro Asp Ser Glu Ile Ala His Tyr Val Ala Gln Ile His Ser
465                 470                 475                 480 aca cga cag aca aag gag ctt tgc gca tga                             1470
Thr Arg Gln Thr Lys Glu Leu Cys Ala
                485
```

```
<210> SEQ ID NO 11
<211> LENGTH: 489
<212> TYPE: PRT
<213> ORGANISM: Escherichia coli

<400> SEQUENCE: 11
```

| | | | | | | | | | | | | | | |
|---|---|---|---|---|---|---|---|---|---|---|---|---|---|---|
| Met | Thr | Phe | Arg | Asn | Cys | Val | Ala | Val | Asp | Leu | Gly | Ala | Ser | Ser | Gly |
| 1 | | | | 5 | | | | | 10 | | | | | 15 | |

| Arg | Val | Met | Leu | Ala | Arg | Tyr | Glu | Arg | Glu | Cys | Arg | Ser | Leu | Thr | Leu |
|---|---|---|---|---|---|---|---|---|---|---|---|---|---|---|---|
| | | | 20 | | | | | 25 | | | | | 30 | | |

| Arg | Glu | Ile | His | Arg | Phe | Asn | Asn | Gly | Leu | His | Ser | Gln | Asn | Gly | Tyr |
|---|---|---|---|---|---|---|---|---|---|---|---|---|---|---|---|
| | | 35 | | | | | 40 | | | | | 45 | | | |

| Val | Thr | Trp | Asp | Val | Asp | Ser | Leu | Glu | Ser | Ala | Ile | Arg | Leu | Gly | Leu |
|---|---|---|---|---|---|---|---|---|---|---|---|---|---|---|---|
| | 50 | | | | | 55 | | | | | 60 | | | | |

| Asn | Lys | Val | Cys | Glu | Glu | Gly | Ile | Arg | Ile | Asp | Ser | Ile | Gly | Ile | Asp |
|---|---|---|---|---|---|---|---|---|---|---|---|---|---|---|---|
| 65 | | | | | 70 | | | | | 75 | | | | | 80 |

| Thr | Trp | Gly | Val | Asp | Phe | Val | Leu | Leu | Asp | Gln | Gly | Gln | Gly | Arg | Val |
|---|---|---|---|---|---|---|---|---|---|---|---|---|---|---|---|
| | | | | 85 | | | | | 90 | | | | | 95 | |

| Gly | Leu | Pro | Val | Ala | Tyr | Arg | Asp | Ser | Arg | Thr | Asn | Gly | Leu | Met | Ala |
|---|---|---|---|---|---|---|---|---|---|---|---|---|---|---|---|
| | | | 100 | | | | | 105 | | | | | 110 | | |

| Gln | Ala | Gln | Gln | Gln | Leu | Gly | Lys | Arg | Asp | Ile | Tyr | Gln | Arg | Ser | Gly |
|---|---|---|---|---|---|---|---|---|---|---|---|---|---|---|---|
| | | 115 | | | | | 120 | | | | | 125 | | | |

| Ile | Gln | Phe | Leu | Pro | Phe | Asn | Thr | Leu | Tyr | Gln | Leu | Arg | Ala | Leu | Thr |
|---|---|---|---|---|---|---|---|---|---|---|---|---|---|---|---|
| | 130 | | | | | 135 | | | | | 140 | | | | |

| Glu | Gln | Gln | Pro | Glu | Leu | Ile | Pro | His | Ile | Ala | His | Ala | Leu | Leu | Met |
|---|---|---|---|---|---|---|---|---|---|---|---|---|---|---|---|
| 145 | | | | | 150 | | | | | 155 | | | | | 160 |

| Pro | Asp | Tyr | Phe | Ser | Tyr | Arg | Leu | Thr | Gly | Lys | Met | Asn | Trp | Glu | Tyr |
|---|---|---|---|---|---|---|---|---|---|---|---|---|---|---|---|
| | | | | 165 | | | | | 170 | | | | | 175 | |

| Thr | Asn | Ala | Thr | Thr | Thr | Gln | Leu | Val | Asn | Ile | Asn | Ser | Asp | Asp | Trp |
|---|---|---|---|---|---|---|---|---|---|---|---|---|---|---|---|
| | | | 180 | | | | | 185 | | | | | 190 | | |

| Asp | Glu | Ser | Leu | Leu | Ala | Trp | Ser | Gly | Ala | Asn | Lys | Ala | Trp | Phe | Gly |
|---|---|---|---|---|---|---|---|---|---|---|---|---|---|---|---|
| | | 195 | | | | | 200 | | | | | 205 | | | |

| Arg | Pro | Thr | His | Pro | Gly | Asn | Val | Ile | Gly | His | Trp | Ile | Cys | Pro | Gln |
|---|---|---|---|---|---|---|---|---|---|---|---|---|---|---|---|
| | 210 | | | | | 215 | | | | | 220 | | | | |

| Gly | Asn | Glu | Ile | Pro | Val | Val | Ala | Val | Ala | Ser | His | Asp | Thr | Ala | Ser |
|---|---|---|---|---|---|---|---|---|---|---|---|---|---|---|---|
| 225 | | | | | 230 | | | | | 235 | | | | | 240 |

| Ala | Val | Ile | Ala | Ser | Pro | Leu | Asn | Gly | Ser | Arg | Ala | Ala | Tyr | Leu | Ser |
|---|---|---|---|---|---|---|---|---|---|---|---|---|---|---|---|
| | | | | 245 | | | | | 250 | | | | | 255 | |

| Ser | Gly | Thr | Trp | Ser | Leu | Met | Gly | Phe | Glu | Ser | Gln | Thr | Pro | Phe | Thr |
|---|---|---|---|---|---|---|---|---|---|---|---|---|---|---|---|
| | | | 260 | | | | | 265 | | | | | 270 | | |

| Asn | Asp | Thr | Ala | Leu | Ala | Ala | Asn | Ile | Thr | Asn | Glu | Gly | Gly | Ala | Glu |
|---|---|---|---|---|---|---|---|---|---|---|---|---|---|---|---|
| | | 275 | | | | | 280 | | | | | 285 | | | |

| Gly | Arg | Tyr | Arg | Val | Leu | Lys | Asn | Ile | Met | Gly | Leu | Trp | Leu | Leu | Gln |
|---|---|---|---|---|---|---|---|---|---|---|---|---|---|---|---|
| | 290 | | | | | 295 | | | | | 300 | | | | |

| Arg | Val | Leu | Gln | Glu | Gln | Gln | Ile | Asn | Asp | Leu | Pro | Ala | Leu | Ile | Ser |
|---|---|---|---|---|---|---|---|---|---|---|---|---|---|---|---|
| 305 | | | | | 310 | | | | | 315 | | | | | 320 |

| Ala | Thr | Gln | Ala | Leu | Pro | Ala | Cys | Arg | Phe | Ile | Ile | Asn | Pro | Asn | Asp |
|---|---|---|---|---|---|---|---|---|---|---|---|---|---|---|---|
| | | | | 325 | | | | | 330 | | | | | 335 | |

| Asp | Arg | Phe | Ile | Asn | Pro | Glu | Thr | Met | Cys | Ser | Glu | Ile | Gln | Ala | Ala |
|---|---|---|---|---|---|---|---|---|---|---|---|---|---|---|---|
| | | | 340 | | | | | 345 | | | | | 350 | | |

| Cys | Arg | Glu | Thr | Ala | Gln | Pro | Ile | Pro | Glu | Ser | Asp | Ala | Glu | Leu | Ala |
|---|---|---|---|---|---|---|---|---|---|---|---|---|---|---|---|
| | | 355 | | | | | 360 | | | | | 365 | | | |

| Arg | Cys | Ile | Phe | Asp | Ser | Leu | Ala | Leu | Leu | Tyr | Ala | Asp | Val | Leu | His |
|---|---|---|---|---|---|---|---|---|---|---|---|---|---|---|---|
| | 370 | | | | | 375 | | | | | 380 | | | | |

```
Glu Leu Ala Gln Leu Arg Gly Glu Asp Phe Ser Gln Leu His Ile Val
385                 390                 395                 400

Gly Gly Gly Cys Gln Asn Thr Leu Leu Asn Gln Leu Cys Ala Asp Ala
            405                 410                 415

Cys Gly Ile Arg Val Ile Ala Gly Pro Val Glu Ala Ser Thr Leu Gly
            420                 425                 430

Asn Ile Gly Ile Gln Leu Met Thr Leu Asp Glu Leu Asn Asn Val Asp
        435                 440                 445

Asp Phe Arg Gln Val Val Ser Thr Thr Ala Asn Leu Thr Thr Phe Thr
    450                 455                 460

Pro Asn Pro Asp Ser Glu Ile Ala His Tyr Val Ala Gln Ile His Ser
465                 470                 475                 480

Thr Arg Gln Thr Lys Glu Leu Cys Ala
                485

<210> SEQ ID NO 12
<211> LENGTH: 825
<212> TYPE: DNA
<213> ORGANISM: Escherichia coli
<220> FEATURE:
<221> NAME/KEY: CDS
<222> LOCATION: (1)..(822)
<223> OTHER INFORMATION: coding for rhaD (rhamnulose-phosphate aldolase)

<400> SEQUENCE: 12 atg caa aac att act cag tcc tgg ttt gtc cag gga atg atc aaa gcc      48
Met Gln Asn Ile Thr Gln Ser Trp Phe Val Gln Gly Met Ile Lys Ala
1               5                   10                  15 acc acc gac gcc tgg ctg aaa ggc tgg gat gag cgc aac ggc ggc aac      96
Thr Thr Asp Ala Trp Leu Lys Gly Trp Asp Glu Arg Asn Gly Gly Asn
            20                  25                  30 ctg acg cta cgc ctg gat gac gcc gat atc gca cca tat cac gac aat     144
Leu Thr Leu Arg Leu Asp Asp Ala Asp Ile Ala Pro Tyr His Asp Asn
        35                  40                  45 ttc cac caa caa ccg cgc tat atc ccg ctc agc cag ccc atg cct tta     192
Phe His Gln Gln Pro Arg Tyr Ile Pro Leu Ser Gln Pro Met Pro Leu
    50                  55                  60 ctg gca aat aca ccg ttt att gtc acc ggc tcg ggc aaa ttc ttc cgt     240
Leu Ala Asn Thr Pro Phe Ile Val Thr Gly Ser Gly Lys Phe Phe Arg
65                  70                  75                  80 aac gtc cag ctt gat cct gcg gct aac tta ggc atc gta aaa gtc gac     288
Asn Val Gln Leu Asp Pro Ala Ala Asn Leu Gly Ile Val Lys Val Asp
                85                  90                  95 agc gac ggc gcg ggc tac cac att ctt tgg ggg tta acc aac gaa gcc     336
Ser Asp Gly Ala Gly Tyr His Ile Leu Trp Gly Leu Thr Asn Glu Ala
            100                 105                 110 gtc ccc act tcc gaa ctt ccg gct cac ttc ctt tcc cac tgc gag cgc     384
Val Pro Thr Ser Glu Leu Pro Ala His Phe Leu Ser His Cys Glu Arg
        115                 120                 125 att aaa gcc acc aac ggc aaa gat cgg gtg atc atg cac tgc cac gcc     432
Ile Lys Ala Thr Asn Gly Lys Asp Arg Val Ile Met His Cys His Ala
    130                 135                 140 acc aac ctg atc gcc ctc acc tat gta ctt gaa aac gac acc gcg gtc     480
Thr Asn Leu Ile Ala Leu Thr Tyr Val Leu Glu Asn Asp Thr Ala Val
145                 150                 155                 160 ttc act cgc caa ctg tgg gaa ggc agc acc gag tgt ctg gtg gta ttc     528
Phe Thr Arg Gln Leu Trp Glu Gly Ser Thr Glu Cys Leu Val Val Phe
                165                 170                 175 ccg gat ggc gtt ggc att ttg ccg tgg atg gtg ccc ggc acg gac gaa     576
Pro Asp Gly Val Gly Ile Leu Pro Trp Met Val Pro Gly Thr Asp Glu
```

```
               180                 185                 190
atc ggc cag gcg acc gca caa gag atg caa aaa cat tcg ctg gtg ttg    624
Ile Gly Gln Ala Thr Ala Gln Glu Met Gln Lys His Ser Leu Val Leu
            195                 200                 205 tgg ccc ttc cac ggc gtc ttc ggc agc gga ccg acg ctg gat gaa acc    672
Trp Pro Phe His Gly Val Phe Gly Ser Gly Pro Thr Leu Asp Glu Thr
210                 215                 220 ttc ggt tta atc gac acc gca gaa aaa tca gca caa gta tta gtg aag    720
Phe Gly Leu Ile Asp Thr Ala Glu Lys Ser Ala Gln Val Leu Val Lys
225                 230                 235                 240 gtt tat tcg atg ggc ggc atg aaa cag acc atc agc cgt gaa gag ttg    768
Val Tyr Ser Met Gly Gly Met Lys Gln Thr Ile Ser Arg Glu Glu Leu
                245                 250                 255 ata gcg ctc ggc aag cgt ttc ggc gtt acg cca ctc gcc agt gcg ctg    816
Ile Ala Leu Gly Lys Arg Phe Gly Val Thr Pro Leu Ala Ser Ala Leu
            260                 265                 270 gcg ctg taa                                                        825
Ala Leu

<210> SEQ ID NO 13
<211> LENGTH: 274
<212> TYPE: PRT
<213> ORGANISM: Escherichia coli

<400> SEQUENCE: 13

Met Gln Asn Ile Thr Gln Ser Trp Phe Val Gln Gly Met Ile Lys Ala
  1               5                  10                  15

Thr Thr Asp Ala Trp Leu Lys Gly Trp Asp Glu Arg Asn Gly Gly Asn
                 20                  25                  30

Leu Thr Leu Arg Leu Asp Asp Ala Asp Ile Ala Pro Tyr His Asp Asn
             35                  40                  45

Phe His Gln Gln Pro Arg Tyr Ile Pro Leu Ser Gln Pro Met Pro Leu
         50                  55                  60

Leu Ala Asn Thr Pro Phe Ile Val Thr Gly Ser Gly Lys Phe Phe Arg
 65                  70                  75                  80

Asn Val Gln Leu Asp Pro Ala Ala Asn Leu Gly Ile Val Lys Val Asp
                 85                  90                  95

Ser Asp Gly Ala Gly Tyr His Ile Leu Trp Gly Leu Thr Asn Glu Ala
            100                 105                 110

Val Pro Thr Ser Glu Leu Pro Ala His Phe Leu Ser His Cys Glu Arg
        115                 120                 125

Ile Lys Ala Thr Asn Gly Lys Asp Arg Val Ile Met His Cys His Ala
    130                 135                 140

Thr Asn Leu Ile Ala Leu Thr Tyr Val Leu Glu Asn Asp Thr Ala Val
145                 150                 155                 160

Phe Thr Arg Gln Leu Trp Glu Gly Ser Thr Glu Cys Leu Val Val Phe
                165                 170                 175

Pro Asp Gly Val Gly Ile Leu Pro Trp Met Val Pro Gly Thr Asp Glu
            180                 185                 190

Ile Gly Gln Ala Thr Ala Gln Glu Met Gln Lys His Ser Leu Val Leu
        195                 200                 205

Trp Pro Phe His Gly Val Phe Gly Ser Gly Pro Thr Leu Asp Glu Thr
    210                 215                 220

Phe Gly Leu Ile Asp Thr Ala Glu Lys Ser Ala Gln Val Leu Val Lys
225                 230                 235                 240

Val Tyr Ser Met Gly Gly Met Lys Gln Thr Ile Ser Arg Glu Glu Leu
```

```
                        245                 250                 255
Ile Ala Leu Gly Lys Arg Phe Gly Val Thr Pro Leu Ala Ser Ala Leu
            260                 265                 270

Ala Leu
```

<210> SEQ ID NO 14
<211> LENGTH: 939
<212> TYPE: DNA
<213> ORGANISM: Escherichia coli
<220> FEATURE:
<221> NAME/KEY: CDS
<222> LOCATION: (1)..(936)
<223> OTHER INFORMATION: coding for rhaR (positive regulator for rhaRS operon)

<400> SEQUENCE: 14

```
atg gct ttc tgc aat aac gcg aat ctt ctc aac gta ttt gta cgc cat      48
Met Ala Phe Cys Asn Asn Ala Asn Leu Leu Asn Val Phe Val Arg His
  1               5                  10                  15 att gcg aat aat caa ctt cgt tct ctg gcc gag gta gcc acg gtg gcg      96
Ile Ala Asn Asn Gln Leu Arg Ser Leu Ala Glu Val Ala Thr Val Ala
                 20                  25                  30 cat cag tta aaa ctt ctc aaa gat gat ttt ttt gcc agc gac cag cag     144
His Gln Leu Lys Leu Leu Lys Asp Asp Phe Phe Ala Ser Asp Gln Gln
             35                  40                  45 gca gtc gct gtg gct gac cgt tat ccg caa gat gtc ttt gct gaa cat     192
Ala Val Ala Val Ala Asp Arg Tyr Pro Gln Asp Val Phe Ala Glu His
         50                  55                  60 aca cat gat ttt tgt gag ctg gtg att gtc tgg cgc ggt aat ggc ctg     240
Thr His Asp Phe Cys Glu Leu Val Ile Val Trp Arg Gly Asn Gly Leu
 65                  70                  75                  80 cat gta ctc aac gat cgc cct tat cgc att acc cgt ggc gat ctc ttt     288
His Val Leu Asn Asp Arg Pro Tyr Arg Ile Thr Arg Gly Asp Leu Phe
                 85                  90                  95 tac att cat gct gac gat aaa cac tcc tac gct tcc gtt aac gat ctg     336
Tyr Ile His Ala Asp Asp Lys His Ser Tyr Ala Ser Val Asn Asp Leu
            100                 105                 110 gtt ttg cag aat att att tat tgc ccg gag cgt ctg aag ctg aat ctt     384
Val Leu Gln Asn Ile Ile Tyr Cys Pro Glu Arg Leu Lys Leu Asn Leu
        115                 120                 125 gac tgg cag ggg gcg att ccg gga ttt aac gcc agc gca ggg caa cca     432
Asp Trp Gln Gly Ala Ile Pro Gly Phe Asn Ala Ser Ala Gly Gln Pro
    130                 135                 140 cac tgg cgc tta ggt agc atg ggg atg gcg cag gcg cgg cag gtt atc     480
His Trp Arg Leu Gly Ser Met Gly Met Ala Gln Ala Arg Gln Val Ile
145                 150                 155                 160 ggt cag ctt gag cat gaa agt agt cag cat gtg ccg ttt gct aac gaa     528
Gly Gln Leu Glu His Glu Ser Ser Gln His Val Pro Phe Ala Asn Glu
                165                 170                 175 atg gct gag ttg ctg ttc ggg cag ttg gtg atg ttg ctg aat cgc cat     576
Met Ala Glu Leu Leu Phe Gly Gln Leu Val Met Leu Leu Asn Arg His
            180                 185                 190 cgt tac acc agt gat tcg ttg ccg cca aca tcc agc gaa acg ttg ctg     624
Arg Tyr Thr Ser Asp Ser Leu Pro Pro Thr Ser Ser Glu Thr Leu Leu
        195                 200                 205 gat aag ctg att acc cgg ctg gcg gct agc ctg aaa agt ccc ttt gcg     672
Asp Lys Leu Ile Thr Arg Leu Ala Ala Ser Leu Lys Ser Pro Phe Ala
    210                 215                 220 ctg gat aaa ttt tgt gat gag gca tcg tgc agt gag cgc gtt ttg cgt     720
Leu Asp Lys Phe Cys Asp Glu Ala Ser Cys Ser Glu Arg Val Leu Arg
225                 230                 235                 240
```

```
cag caa ttt cgc cag cag act gga atg acc atc aat caa tat ctg cga    768
Gln Gln Phe Arg Gln Gln Thr Gly Met Thr Ile Asn Gln Tyr Leu Arg
            245                 250                 255 cag gtc aga gtg tgt cat gcg caa tat ctt ctc cag cat agc cgc ctg    816
Gln Val Arg Val Cys His Ala Gln Tyr Leu Leu Gln His Ser Arg Leu
260                 265                 270 tta atc agt gat att tcg acc gaa tgt ggc ttt gaa gat agt aac tat    864
Leu Ile Ser Asp Ile Ser Thr Glu Cys Gly Phe Glu Asp Ser Asn Tyr
    275                 280                 285 ttt tcg gtg gtg ttt acc cgg gaa acc ggg atg acg ccc agc cag tgg    912
Phe Ser Val Val Phe Thr Arg Glu Thr Gly Met Thr Pro Ser Gln Trp
290                 295                 300 cgt cat ctc aat tcg cag aaa gat taa                                939
Arg His Leu Asn Ser Gln Lys Asp
305             310
```

<210> SEQ ID NO 15
<211> LENGTH: 312
<212> TYPE: PRT
<213> ORGANISM: Escherichia coli

<400> SEQUENCE: 15

```
Met Ala Phe Cys Asn Asn Ala Asn Leu Leu Asn Val Phe Val Arg His
1               5                   10                  15

Ile Ala Asn Asn Gln Leu Arg Ser Leu Ala Glu Val Ala Thr Val Ala
            20                  25                  30

His Gln Leu Lys Leu Leu Lys Asp Asp Phe Phe Ala Ser Asp Gln Gln
        35                  40                  45

Ala Val Ala Val Ala Asp Arg Tyr Pro Gln Asp Val Phe Ala Glu His
    50                  55                  60

Thr His Asp Phe Cys Glu Leu Val Ile Val Trp Arg Gly Asn Gly Leu
65                  70                  75                  80

His Val Leu Asn Asp Arg Pro Tyr Arg Ile Thr Arg Gly Asp Leu Phe
                85                  90                  95

Tyr Ile His Ala Asp Asp Lys His Ser Tyr Ala Ser Val Asn Asp Leu
            100                 105                 110

Val Leu Gln Asn Ile Ile Tyr Cys Pro Glu Arg Leu Lys Leu Asn Leu
        115                 120                 125

Asp Trp Gln Gly Ala Ile Pro Gly Phe Asn Ala Ser Ala Gly Gln Pro
    130                 135                 140

His Trp Arg Leu Gly Ser Met Gly Met Ala Gln Ala Arg Gln Val Ile
145                 150                 155                 160

Gly Gln Leu Glu His Glu Ser Ser Gln His Val Pro Phe Ala Asn Glu
                165                 170                 175

Met Ala Glu Leu Leu Phe Gly Gln Leu Val Met Leu Leu Asn Arg His
            180                 185                 190

Arg Tyr Thr Ser Asp Ser Leu Pro Pro Thr Ser Ser Glu Thr Leu Leu
        195                 200                 205

Asp Lys Leu Ile Thr Arg Leu Ala Ala Ser Leu Lys Ser Pro Phe Ala
    210                 215                 220

Leu Asp Lys Phe Cys Asp Glu Ala Ser Cys Ser Glu Arg Val Leu Arg
225                 230                 235                 240

Gln Gln Phe Arg Gln Gln Thr Gly Met Thr Ile Asn Gln Tyr Leu Arg
                245                 250                 255

Gln Val Arg Val Cys His Ala Gln Tyr Leu Leu Gln His Ser Arg Leu
            260                 265                 270
```

```
Leu Ile Ser Asp Ile Ser Thr Glu Cys Gly Phe Glu Asp Ser Asn Tyr
            275                 280                 285

Phe Ser Val Val Phe Thr Arg Glu Thr Gly Met Thr Pro Ser Gln Trp
    290                 295                 300

Arg His Leu Asn Ser Gln Lys Asp
305                 310

<210> SEQ ID NO 16
<211> LENGTH: 837
<212> TYPE: DNA
<213> ORGANISM: Escherichia coli
<220> FEATURE:
<221> NAME/KEY: CDS
<222> LOCATION: (1)..(834)
<223> OTHER INFORMATION: coding for rhaS (positive regulator of rhaBAD
      operon)

<400> SEQUENCE: 16 atg acc gta tta cat agt gtg gat ttt ttt ccg tct ggt aac gcg tcc      48
Met Thr Val Leu His Ser Val Asp Phe Phe Pro Ser Gly Asn Ala Ser
  1               5                  10                  15 gtg gcg ata gaa ccc cgg ctc ccg cag gcg gat ttt cct gaa cat cat      96
Val Ala Ile Glu Pro Arg Leu Pro Gln Ala Asp Phe Pro Glu His His
             20                  25                  30 cat gat ttt cat gaa att gtg att gtc gaa cat ggc acg ggt att cat    144
His Asp Phe His Glu Ile Val Ile Val Glu His Gly Thr Gly Ile His
         35                  40                  45 gtg ttt aat ggg cag ccc tat acc atc acc ggt ggc acg gtc tgt ttc    192
Val Phe Asn Gly Gln Pro Tyr Thr Ile Thr Gly Gly Thr Val Cys Phe
     50                  55                  60 gta cgc gat cat gat cgg cat ctg tat gaa cat acc gat aat ctg tgt    240
Val Arg Asp His Asp Arg His Leu Tyr Glu His Thr Asp Asn Leu Cys
 65                  70                  75                  80 ctg acc aat gtg ctg tat cgc tcg ccg gat cga ttt cag ttt ctc gcc    288
Leu Thr Asn Val Leu Tyr Arg Ser Pro Asp Arg Phe Gln Phe Leu Ala
                 85                  90                  95 ggg ctg aat cag ttg ctg cca caa gag ctg gat ggg cag tat ccg tct    336
Gly Leu Asn Gln Leu Leu Pro Gln Glu Leu Asp Gly Gln Tyr Pro Ser
            100                 105                 110 cac tgg cgc gtt aac cac agc gta ttg cag cag gtg cga cag ctg gtt    384
His Trp Arg Val Asn His Ser Val Leu Gln Gln Val Arg Gln Leu Val
        115                 120                 125 gca cag atg gaa cag cag gaa ggg gaa aat gat tta ccc tcg acc gcc    432
Ala Gln Met Glu Gln Gln Glu Gly Glu Asn Asp Leu Pro Ser Thr Ala
    130                 135                 140 agt cgc gag atc ttg ttt atg caa tta ctg ctc ttg ctg cgt aaa agc    480
Ser Arg Glu Ile Leu Phe Met Gln Leu Leu Leu Leu Leu Arg Lys Ser
145                 150                 155                 160 agt ttg cag gag aac ctg gaa aac agc gca tca cgt ctc aac ttg ctt    528
Ser Leu Gln Glu Asn Leu Glu Asn Ser Ala Ser Arg Leu Asn Leu Leu
                165                 170                 175 ctg gcc tgg ctg gag gac cat ttt gcc gat gag gtg aat tgg gat gcc    576
Leu Ala Trp Leu Glu Asp His Phe Ala Asp Glu Val Asn Trp Asp Ala
            180                 185                 190 gtg gcg gat caa ttt tct ctt tca ctg cgt acg cta cat cgg cag ctt    624
Val Ala Asp Gln Phe Ser Leu Ser Leu Arg Thr Leu His Arg Gln Leu
        195                 200                 205 aag cag caa acg gga ctg acg cct cag cga tac ctg aac cgc ctg cga    672
Lys Gln Gln Thr Gly Leu Thr Pro Gln Arg Tyr Leu Asn Arg Leu Arg
    210                 215                 220
```

```
ctg atg aaa gcc cga cat ctg cta cgc cac agc gag gcc agc gtt act      720
Leu Met Lys Ala Arg His Leu Leu Arg His Ser Glu Ala Ser Val Thr
225                 230                 235                 240 gac atc gcc tat cgc tgt gga ttc agc gac agt aac cac ttt tcg acg      768
Asp Ile Ala Tyr Arg Cys Gly Phe Ser Asp Ser Asn His Phe Ser Thr
            245                 250                 255 ctt ttt cgc cga gag ttt aac tgg tca ccg cgt gat att cgc cag gga      816
Leu Phe Arg Arg Glu Phe Asn Trp Ser Pro Arg Asp Ile Arg Gln Gly
        260                 265                 270 cgg gat ggc ttt ctg caa taa                                          837
Arg Asp Gly Phe Leu Gln
        275
```

<210> SEQ ID NO 17
<211> LENGTH: 278
<212> TYPE: PRT
<213> ORGANISM: Escherichia coli

<400> SEQUENCE: 17

```
Met Thr Val Leu His Ser Val Asp Phe Pro Ser Gly Asn Ala Ser
 1               5                  10                  15

Val Ala Ile Glu Pro Arg Leu Pro Gln Ala Asp Phe Pro Glu His His
                20                  25                  30

His Asp Phe His Glu Ile Val Ile Val Glu His Gly Thr Gly Ile His
            35                  40                  45

Val Phe Asn Gly Gln Pro Tyr Thr Ile Thr Gly Gly Thr Val Cys Phe
    50                  55                  60

Val Arg Asp His Asp Arg His Leu Tyr Glu His Thr Asp Asn Leu Cys
65                  70                  75                  80

Leu Thr Asn Val Leu Tyr Arg Ser Pro Asp Arg Phe Gln Phe Leu Ala
                85                  90                  95

Gly Leu Asn Gln Leu Leu Pro Gln Glu Leu Asp Gly Gln Tyr Pro Ser
            100                 105                 110

His Trp Arg Val Asn His Ser Val Leu Gln Gln Val Arg Gln Leu Val
        115                 120                 125

Ala Gln Met Glu Gln Gln Glu Gly Glu Asn Asp Leu Pro Ser Thr Ala
    130                 135                 140

Ser Arg Glu Ile Leu Phe Met Gln Leu Leu Leu Leu Arg Lys Ser
145                 150                 155                 160

Ser Leu Gln Glu Asn Leu Glu Asn Ser Ala Ser Arg Leu Asn Leu Leu
                165                 170                 175

Leu Ala Trp Leu Glu Asp His Phe Ala Asp Glu Val Asn Trp Asp Ala
            180                 185                 190

Val Ala Asp Gln Phe Ser Leu Ser Leu Arg Thr Leu His Arg Gln Leu
        195                 200                 205

Lys Gln Gln Thr Gly Leu Thr Pro Gln Arg Tyr Leu Asn Arg Leu Arg
    210                 215                 220

Leu Met Lys Ala Arg His Leu Leu Arg His Ser Glu Ala Ser Val Thr
225                 230                 235                 240

Asp Ile Ala Tyr Arg Cys Gly Phe Ser Asp Ser Asn His Phe Ser Thr
                245                 250                 255

Leu Phe Arg Arg Glu Phe Asn Trp Ser Pro Arg Asp Ile Arg Gln Gly
            260                 265                 270

Arg Asp Gly Phe Leu Gln
        275
```

<210> SEQ ID NO 18
<211> LENGTH: 1035
<212> TYPE: DNA
<213> ORGANISM: Escherichia coli
<220> FEATURE:
<221> NAME/KEY: CDS
<222> LOCATION: (1)..(1032)
<223> OTHER INFORMATION: coding for rhaT (rhamnose transport protein)

<400> SEQUENCE: 18

| | | | | | | | | | | | | | | | | |
|---|---|---|---|---|---|---|---|---|---|---|---|---|---|---|---|---|
| atg | agt | aac | gcg | att | acg | atg | ggg | ata | ttt | tgg | cat | ttg | atc | ggc | gcg | 48 |
| Met | Ser | Asn | Ala | Ile | Thr | Met | Gly | Ile | Phe | Trp | His | Leu | Ile | Gly | Ala | |
| 1 | | | | 5 | | | | | 10 | | | | | 15 | | |
| gcc | agt | gca | gcc | tgt | ttt | tac | gct | ccg | ttc | aaa | aaa | gta | aaa | aaa | tgg | 96 |
| Ala | Ser | Ala | Ala | Cys | Phe | Tyr | Ala | Pro | Phe | Lys | Lys | Val | Lys | Lys | Trp | |
| | | | 20 | | | | | 25 | | | | | 30 | | | |
| tca | tgg | gaa | acc | atg | tgg | tca | gtc | ggt | ggg | att | gtt | tcg | tgg | att | att | 144 |
| Ser | Trp | Glu | Thr | Met | Trp | Ser | Val | Gly | Gly | Ile | Val | Ser | Trp | Ile | Ile | |
| | | 35 | | | | | 40 | | | | | 45 | | | | |
| ctg | ccg | tgg | gcc | atc | agc | gcc | ctg | tta | cta | ccg | aat | ttc | tgg | gcg | tat | 192 |
| Leu | Pro | Trp | Ala | Ile | Ser | Ala | Leu | Leu | Leu | Pro | Asn | Phe | Trp | Ala | Tyr | |
| | 50 | | | | | 55 | | | | | 60 | | | | | |
| tac | agc | tcg | ttt | agt | ctc | tct | acg | cga | ctg | cct | gtt | ttt | ctg | ttc | ggc | 240 |
| Tyr | Ser | Ser | Phe | Ser | Leu | Ser | Thr | Arg | Leu | Pro | Val | Phe | Leu | Phe | Gly | |
| 65 | | | | | 70 | | | | | 75 | | | | | 80 | |
| gct | atg | tgg | ggg | atc | ggt | aat | atc | aac | tac | ggc | ctg | acc | atg | cgt | tat | 288 |
| Ala | Met | Trp | Gly | Ile | Gly | Asn | Ile | Asn | Tyr | Gly | Leu | Thr | Met | Arg | Tyr | |
| | | | | 85 | | | | | 90 | | | | | 95 | | |
| ctc | ggc | atg | tcg | atg | gga | att | ggc | atc | gcc | att | ggc | att | acg | ttg | att | 336 |
| Leu | Gly | Met | Ser | Met | Gly | Ile | Gly | Ile | Ala | Ile | Gly | Ile | Thr | Leu | Ile | |
| | | | 100 | | | | | 105 | | | | | 110 | | | |
| gtc | ggt | acg | ctg | atg | acg | cca | att | atc | aac | ggc | aat | ttc | gat | gtg | ttg | 384 |
| Val | Gly | Thr | Leu | Met | Thr | Pro | Ile | Ile | Asn | Gly | Asn | Phe | Asp | Val | Leu | |
| | | 115 | | | | | 120 | | | | | 125 | | | | |
| att | agc | acc | gaa | ggc | gga | cgc | atg | acg | ttg | ctc | ggc | gtt | ctg | gtg | gcg | 432 |
| Ile | Ser | Thr | Glu | Gly | Gly | Arg | Met | Thr | Leu | Leu | Gly | Val | Leu | Val | Ala | |
| | 130 | | | | | 135 | | | | | 140 | | | | | |
| ctg | att | ggc | gta | ggg | att | gta | act | cgc | gcc | ggg | cag | ttg | aaa | gag | cgc | 480 |
| Leu | Ile | Gly | Val | Gly | Ile | Val | Thr | Arg | Ala | Gly | Gln | Leu | Lys | Glu | Arg | |
| 145 | | | | | 150 | | | | | 155 | | | | | 160 | |
| aag | atg | ggc | att | aaa | gcc | gaa | gag | ttc | aat | ctg | aaa | aaa | ggg | ctg | gtg | 528 |
| Lys | Met | Gly | Ile | Lys | Ala | Glu | Glu | Phe | Asn | Leu | Lys | Lys | Gly | Leu | Val | |
| | | | | 165 | | | | | 170 | | | | | 175 | | |
| ctg | gcg | gtg | atg | tgc | ggc | att | ttc | tct | gcc | ggg | atg | tcc | ttt | gcg | atg | 576 |
| Leu | Ala | Val | Met | Cys | Gly | Ile | Phe | Ser | Ala | Gly | Met | Ser | Phe | Ala | Met | |
| | | | 180 | | | | | 185 | | | | | 190 | | | |
| aac | gcc | gca | aaa | ccg | atg | cat | gaa | gcc | gct | gcc | gca | ctt | ggc | gtc | gat | 624 |
| Asn | Ala | Ala | Lys | Pro | Met | His | Glu | Ala | Ala | Ala | Ala | Leu | Gly | Val | Asp | |
| | | 195 | | | | | 200 | | | | | 205 | | | | |
| cca | ctg | tat | gtc | gct | ctg | cca | agc | tat | gtt | gtc | atc | atg | ggc | ggc | ggc | 672 |
| Pro | Leu | Tyr | Val | Ala | Leu | Pro | Ser | Tyr | Val | Val | Ile | Met | Gly | Gly | Gly | |
| | 210 | | | | | 215 | | | | | 220 | | | | | |
| gcg | atc | att | aac | ctc | ggt | ttc | tgt | ttt | att | cgt | ctg | gca | aaa | gtg | aag | 720 |
| Ala | Ile | Ile | Asn | Leu | Gly | Phe | Cys | Phe | Ile | Arg | Leu | Ala | Lys | Val | Lys | |
| 225 | | | | | 230 | | | | | 235 | | | | | 240 | |
| gat | ttg | tcg | cta | aaa | gcc | gac | ttc | tcg | ctg | gca | aaa | tcg | ctg | atc | att | 768 |
| Asp | Leu | Ser | Leu | Lys | Ala | Asp | Phe | Ser | Leu | Ala | Lys | Ser | Leu | Ile | Ile | |
| | | | | 245 | | | | | 250 | | | | | 255 | | |
| cac | aat | gtg | tta | ctc | tcg | aca | ctg | ggc | ggg | ttg | atg | tgg | tat | ctg | caa | 816 |
| His | Asn | Val | Leu | Leu | Ser | Thr | Leu | Gly | Gly | Leu | Met | Trp | Tyr | Leu | Gln | |
| | | | 260 | | | | | 265 | | | | | 270 | | | |

```
ttc ttt ttc tat gcc tgg ggc cac gcc cgt att ccg gcg cag tat gac      864
Phe Phe Phe Tyr Ala Trp Gly His Ala Arg Ile Pro Ala Gln Tyr Asp
        275                 280                 285 tac atc agt tgg atg ctg cat atg agt ttc tat gta ttg tgc ggc ggt      912
Tyr Ile Ser Trp Met Leu His Met Ser Phe Tyr Val Leu Cys Gly Gly
290                 295                 300 atc gtc ggg ctg gtg ctg aaa gag tgg aac aat gca gga cgc cgt ccg      960
Ile Val Gly Leu Val Leu Lys Glu Trp Asn Asn Ala Gly Arg Arg Pro
305                 310                 315                 320 gta acg gtg ttg agc ctc ggt tgt gtg gtg att att gtc gcc gct aac     1008
Val Thr Val Leu Ser Leu Gly Cys Val Val Ile Ile Val Ala Ala Asn
            325                 330                 335 atc gtc ggc atc ggc atg gcg aat taa                                 1035
Ile Val Gly Ile Gly Met Ala Asn
340
```

<210> SEQ ID NO 19
<211> LENGTH: 344
<212> TYPE: PRT
<213> ORGANISM: Escherichia coli

<400> SEQUENCE: 19

```
Met Ser Asn Ala Ile Thr Met Gly Ile Phe Trp His Leu Ile Gly Ala
1               5                   10                  15

Ala Ser Ala Ala Cys Phe Tyr Ala Pro Phe Lys Lys Val Lys Lys Trp
            20                  25                  30

Ser Trp Glu Thr Met Trp Ser Val Gly Gly Ile Val Ser Trp Ile Ile
        35                  40                  45

Leu Pro Trp Ala Ile Ser Ala Leu Leu Leu Pro Asn Phe Trp Ala Tyr
    50                  55                  60

Tyr Ser Ser Phe Ser Leu Ser Thr Arg Leu Pro Val Phe Leu Phe Gly
65                  70                  75                  80

Ala Met Trp Gly Ile Gly Asn Ile Asn Tyr Gly Leu Thr Met Arg Tyr
                85                  90                  95

Leu Gly Met Ser Met Gly Ile Gly Ile Ala Ile Gly Ile Thr Leu Ile
            100                 105                 110

Val Gly Thr Leu Met Thr Pro Ile Ile Asn Gly Asn Phe Asp Val Leu
        115                 120                 125

Ile Ser Thr Glu Gly Gly Arg Met Thr Leu Leu Gly Val Leu Val Ala
    130                 135                 140

Leu Ile Gly Val Gly Ile Val Thr Arg Ala Gly Gln Leu Lys Glu Arg
145                 150                 155                 160

Lys Met Gly Ile Lys Ala Glu Glu Phe Asn Leu Lys Lys Gly Leu Val
                165                 170                 175

Leu Ala Val Met Cys Gly Ile Phe Ser Ala Gly Met Ser Phe Ala Met
            180                 185                 190

Asn Ala Ala Lys Pro Met His Glu Ala Ala Ala Leu Gly Val Asp
        195                 200                 205

Pro Leu Tyr Val Ala Leu Pro Ser Tyr Val Val Ile Met Gly Gly Gly
    210                 215                 220

Ala Ile Ile Asn Leu Gly Phe Cys Phe Ile Arg Leu Ala Lys Val Lys
225                 230                 235                 240

Asp Leu Ser Leu Lys Ala Asp Phe Ser Leu Ala Lys Ser Leu Ile Ile
                245                 250                 255

His Asn Val Leu Leu Ser Thr Leu Gly Gly Leu Met Trp Tyr Leu Gln
            260                 265                 270
```

```
Phe Phe Phe Tyr Ala Trp Gly His Ala Arg Ile Pro Ala Gln Tyr Asp
            275                 280                 285

Tyr Ile Ser Trp Met Leu His Met Ser Phe Tyr Val Leu Cys Gly Gly
            290                 295                 300

Ile Val Gly Leu Val Leu Lys Glu Trp Asn Asn Ala Gly Arg Arg Pro
305                 310                 315                 320

Val Thr Val Leu Ser Leu Gly Cys Val Val Ile Val Ala Ala Asn
                325                 330                 335

Ile Val Gly Ile Gly Met Ala Asn
            340
```

<210> SEQ ID NO 20
<211> LENGTH: 31
<212> TYPE: DNA
<213> ORGANISM: Artificial Sequence
<220> FEATURE:
<223> OTHER INFORMATION: MKe258 Primer

<400> SEQUENCE: 20
cccaagcttg gatcatgttt gctccttaca g        31

<210> SEQ ID NO 21
<211> LENGTH: 30
<212> TYPE: DNA
<213> ORGANISM: Artificial Sequence
<220> FEATURE:
<223> OTHER INFORMATION: MKe259 Primer

<400> SEQUENCE: 21
gcgaattcgc atgaccactc aactggaaca          30

<210> SEQ ID NO 22
<211> LENGTH: 30
<212> TYPE: DNA
<213> ORGANISM: Artificial Sequence
<220> FEATURE:
<223> OTHER INFORMATION: MKe260 Primer

<400> SEQUENCE: 22
cccaagctta cccgcggcga ctcaaaattt          30

<210> SEQ ID NO 23
<211> LENGTH: 36
<212> TYPE: DNA
<213> ORGANISM: Artificial Sequence
<220> FEATURE:
<223> OTHER INFORMATION: MKe001 Primer

<400> SEQUENCE: 23
ataagaatgc ggccgcatga ccactcaact ggaaca    36

<210> SEQ ID NO 24
<211> LENGTH: 29
<212> TYPE: DNA
<213> ORGANISM: Artificial Sequence
<220> FEATURE:
<223> OTHER INFORMATION: MKe002

<400> SEQUENCE: 24
ctagctctag attacccgcg gcgactcaa           29